United States Patent
Muhammad et al.

(10) Patent No.: US 9,951,001 B2
(45) Date of Patent: Apr. 24, 2018

(54) HEPATOPROTECTANT ACETAMINOPHEN MUTUAL PRODRUGS

(71) Applicant: Acorda Therapeutics, Inc., Ardsley, NY (US)

(72) Inventors: Naweed Muhammad, Fremont, CA (US); Keith R. Bley, Menlo Park, CA (US); Jeffrey Tobias, San Francisco, CA (US)

(73) Assignee: Acorda Therapeutics, Inc., Ardsley, NY (US)

( * ) Notice: Subject to any disclaimer, the term of this patent is extended or adjusted under 35 U.S.C. 154(b) by 0 days.

(21) Appl. No.: 15/150,099

(22) Filed: May 9, 2016

(65) Prior Publication Data

US 2016/0326107 A1    Nov. 10, 2016

Related U.S. Application Data

(63) Continuation of application No. 12/993,091, filed as application No. PCT/US2009/044749 on May 20, 2009, now abandoned.

(60) Provisional application No. 61/054,777, filed on May 20, 2008.

(51) Int. Cl.
| C07C 323/52 | (2006.01) |
| A61K 31/195 | (2006.01) |
| A61K 31/485 | (2006.01) |
| A61K 45/06 | (2006.01) |
| A61K 9/00 | (2006.01) |
| A61K 31/216 | (2006.01) |

(52) U.S. Cl.
CPC .......... *C07C 323/52* (2013.01); *A61K 9/0053* (2013.01); *A61K 31/195* (2013.01); *A61K 31/216* (2013.01); *A61K 31/485* (2013.01); *A61K 45/06* (2013.01)

(58) Field of Classification Search
None
See application file for complete search history.

(56) References Cited

U.S. PATENT DOCUMENTS

| 4,035,507 A | 7/1977 | Bodor et al. |
| 4,181,719 A | 1/1980 | Margetts et al. |
| 4,361,703 A | 11/1982 | Margetts et al. |
| 4,405,800 A | 9/1983 | Margetts et al. |
| 4,482,495 A | 11/1984 | Margetts et al. |
| 4,562,024 A | 12/1985 | Rogerson |
| 4,567,192 A | 1/1986 | Révész et al. |
| 5,001,115 A | 3/1991 | Sloan |
| 5,474,757 A | 12/1995 | Yang |
| 5,916,910 A | 6/1999 | Lai |
| 6,710,086 B1 | 3/2004 | Lai et al. |
| 6,989,452 B2 | 1/2006 | Ng et al. |
| 7,338,962 B2 | 3/2008 | Dolle et al. |
| 2003/0022876 A1 | 1/2003 | Ashton et al. |
| 2003/0073618 A1 | 4/2003 | Kozhemyakin et al. |
| 2003/0073852 A1 | 4/2003 | Ng et al. |
| 2003/0118528 A1 | 6/2003 | Walters et al. |
| 2003/0170286 A1 | 9/2003 | Ashton et al. |
| 2003/0203030 A1 | 10/2003 | Ashton et al. |
| 2004/0058946 A1 | 3/2004 | Buchwald et al. |
| 2004/0186135 A1 | 9/2004 | Dolle et al. |
| 2005/0113295 A1 | 5/2005 | Dolle |
| 2005/0159438 A1 | 7/2005 | Dolle et al. |
| 2005/0164994 A1 | 7/2005 | Ashton et al. |
| 2005/0272798 A1 | 12/2005 | Ng et al. |
| 2006/0046967 A1 | 3/2006 | Satyam |
| 2006/0205674 A2 | 9/2006 | Satyam |
| 2006/0270695 A1 | 11/2006 | Dolle et al. |
| 2006/0276676 A1 | 12/2006 | van Bommel et al. |
| 2007/0082041 A1 | 4/2007 | Walters et al. |
| 2007/0117827 A1 | 5/2007 | Tollefson et al. |
| 2007/0225277 A1 | 9/2007 | Rosenzweig-Lipson |
| 2008/0102031 A1 | 5/2008 | Dolle et al. |
| 2008/0107720 A1 | 5/2008 | Walters et al. |
| 2008/0318905 A1 | 12/2008 | Muhammad et al. |
| 2011/0263545 A1 | 10/2011 | Muhammad et al. |

FOREIGN PATENT DOCUMENTS

| DE | 43 27 462 A1 | 2/1995 |
| GB | 1 583 602 A | 1/1981 |
| GB | 2 139 225 A | 11/1984 |
| JP | S59-206371 A | 11/1984 |
| WO | WO-01/68069 A2 | 9/2001 |
| WO | WO-01/68069 A3 | 9/2001 |
| WO | WO-01/68609 A1 | 9/2001 |
| WO | WO-02/30866 A1 | 4/2002 |
| WO | WO-2009/143295 A1 | 11/2009 |
| WO | WO-2009/143297 A1 | 11/2009 |
| WO | WO-2009/143299 A1 | 11/2009 |

OTHER PUBLICATIONS

English translation of DE 4327462 (1995).*

(Continued)

*Primary Examiner* — Bong-Sook Baek

(74) *Attorney, Agent, or Firm* — Morrison & Foerster LLP

(57) ABSTRACT

The present invention provides hepatoprotectant acetaminophen mutual prodrugs, which have an acetaminophen moiety covalently linked to a second moiety that may act as a hepatoprotectant against acetaminophen hepatotoxicity. Additionally, acetaminophen mutual prodrugs may have improved water solubility which may provide better suitability for parenteral and other dosage forms relative to administration of acetaminophen. Also provided are methods of treating a disease or condition that is responsive to acetaminophen (such as fever, pain and ischemic injury) using hepatoprotectant acetaminophen mutual prodrugs, as well as kits and unit dosages.

9 Claims, 5 Drawing Sheets

(56) References Cited

OTHER PUBLICATIONS

Bisaglia, M. et al. (2002). "Acetaminophen Protects Hippocampal Neurons and PC12 Cultures from Amyloid β-Peptides Induced Oxidative Stress and Reduces NF-κB Activation," *Neurochem. Int.* 41:43-54.

Bridger, S. et al. (Jun. 6, 1998). "Deaths from Low Dose Paracetamol Poisoning," *BMJ* 316:1724-1725.

Clements, J.A. et al. (1984). "The Role of Sulfate Conjugation in the Metabolism and Disposition of Oral and Intravenous Paracetamol in Man," *British Journal of Clinical Pharmacology* 18:481-485.

Coen, M. et al. (2003, e-pub. Jan. 23, 2003). "An Integrated Metabonomic Investigation of Acetaminophen Toxicity in the Mouse Using NMR Spectroscopy," *Chemical Research in Toxicology* 16(3):295-303.

Crankshaw, D.L. et al. (2002). "Double-Prodrugs of L -Cysteine: Differential Protection Against Acetaminophen-Induced Hepatoxicity in Mice," *J. Biochem. Molecular Toxicology* 16(5):235-244.

Critchley, J.A.J.H. et al. (1981). "Paracetamol Metabolism in Heavy Drinkers," *Proceedings of the British Pharmacological Society*, University of Oxford, Sep. 16-18, 1981, pp. 276P-277P.

Critchley, J.A.J.H. et al. (1986). "Inter-Subject and Ethnic Differences in Paracetamol Metabolism," *British Journal of Clinical Pharmacology* 22:649-657.

Crome, P. et al. (Oct. 16, 1976). "Oral Methionine in the Treatment of Severe Paracetamol (Acetaminophen) Overdose," *Lancet* 2(7990):829-830.

Cumberland Pharmaceuticals. (Mar. 2004). "Acetadote ® (Acetylcysteine) Injection," Package Insert, 2 pages.

Dipiro, J.T. et al. eds. (2005). "Section 1. Basic Concepts," in "Clinical Toxicology," Chapter 10 in *Pharmacotherapy: A Physiological Approach*, $6^{th}$ Edition, McGraw Hill: New York, pp. 132-135.

Douidar, S.M. et al. (1987). "A Novel Mechanism for the Enhancement of Acetaminophen Hepatotoxicity by Phenobarbital," *Journal of Pharmacology and Experimental Therapeutics* 240(2):578-583.

Evans, D.A. et al. (1990). "The Asymmetric Synthesis of α-Amino Acids. Electrophilic Azidation of Chrial Imide Enolates, a Practical Approach to the Synthesis of (R)- and (S)- α-Azido Carboxylic Acids," *J. Amer. Chem. Soc.* 112(10):4011-4030.

Evans, G. (2004) "A Handbook of Bioanalysis and Drug Metabolism, 14.2.4 Acetylation," p. 228-229.

Final Office Action dated Nov. 10, 2015, for U.S. Appl. No. 12/993,091, filed Apr. 21, 2011, 13 pages.

Forrest, J.A.H. et al. (1979). "Paracetamol Metabolism in Chronic Liver Disease," *European Journal of Clinical Pharmacology* 15:427-431.

Grafström, R. et al. (1979). "Paracetamol Metabolism in the Isolated Perfused Rat Liver with Further Metabolism of a Biliary Paracetamol Conjugate by the Small Intestine," *Biochemical Pharmacology* 28:3573-3579.

Green, M.D. et al. (1981). "Age- and Sex-Related Differences in Acetaminophen Metabolism in the Rat," *Life Sciences* 29(23):2421-2428.

Harvard Medical School (Mar. 2006). "Avoiding Acetaminophen-Related Liver Injury," *Harvard Women's Health Watch* 13(7):1-2.

Howland, MA. (2002). "Antidotes in Depth," in "Acteaminophen," Chapter 32 in *Goldfrank's Toxicologic Emergencies*, $7^{th}$ Edition, McGraw Hill: New York, NY, pp. 502-506.

International Search Report dated Jul. 21, 2009, for PCT Patent Application No. PCT/US09/44749, filed on May 20, 2009, 1 page.

James, L.P. et al. (2003). "Acetamniophen-Induced Hepatotoxicity," *Drug Metabolism and Disposition* 31(12):1499-1506.

Jollow, D.J. et al. (1982). "Biochemical Basis for Dose Response Relationships in Reactive Metabolite Toxicity," in *Biological Reactive Intermediates-II , Chemical Mechanisms and Biological Effects*, Part A, Snyder, R. et al. eds., Penum Press: New York, NY, pp. 99-113.

Jones, A.L. et al. (Aug. 2, 1997). "Controversies in Management. Should Methionine be Added to Every Paracetamol Tablet?" *BMJ* 315:301-304.

Jones, D.P. et al. (Apr. 25, 1979). "Metabolism of Glutathione and a Glutathione Conjugate by Isolated Kidney Cells," *The Journal of Biological Chemistry* 254(8):2787-2792.

Krise, J.P. et al. (Aug. 12, 1999, e-pub. Jul. 17, 1999). "Novel Prodrug Approach for Tertiary Amines: Synthesis and Preliminary Evaluation of N-Phosphonooxymethyl Prodrugs," *Journal of Medicinal Chemistry* 42(16) :3094-3100.

Lauterburg, B.H. et al. (1982). "Toxic Doses of Acetaminophen Suppress Hepatic Glutathione Synthesis in Rats," *Hepatology* 2(1):8-12.

Lee, W.M. (Jul. 2004). "Acetaminophen and the U.S. Acute Liver Failure Study Group: Lowering the Risks of Hepatic Failure," *Hepatology* 40(1):6-9.

Letteron, P. et al. (1986). "Pre- or Post- Treatment with Methoxsalen Prevents the Hepatoxicity of Acetaminophen in Mice," *Journal of Pharmacology and Experimental Therapeutics* 239(2):559-567.

Lynch, R.M. et al. (2004). "Anaphylactoid Reactions to Intravenous N-Acetylcysteine: A Prospective Case Controlled Study," *Accid. Emerg. Nurs.* 12:10-15.

Mineshita, S. et al. (Dec. 1983). "Determination of Phenacetin and Its Metabolites in Human Urine and Plasma by High-Performance Liquid Chromatography," *Rinsho Yakuri* 14(4):613-620.

Mineshita, S. et al. (1986). "Determination of Phenacetin and Its Major Matabolites in Human Plasma and Urine by High-Performance Liquid Chromatography," *Journal of Chromatography* 380:407-413.

Mudd, S.H. et al. (1982). "Disorders of Transsulfuration," Chapter 25 in *The Metabolic Bases of Inherited Disease*, $5^{th}$ Edition, Stanbury J.B. et al. eds., McGraw-Hill Book Company: New York, NY, pp. 522-559.

Mutlib, A.E. et al. (2000). "Disposition of Glutathione Conjugates in Rats by a Novel Glutamic Acid Pathway: Characterization of Unique Peptide Conjugates by Liquid Chromatography/Mass Spectrometry and Liquid Chromatography/NMR," *The Journal of Pharmacology and Experimental Therapeutics* 294(2):735-745.

Netdoctor (Aug. 7, 2004). "Paradote," located at <http://www.netdoctor.co.uk/medicines/100002010.html>, last visited on May 12, 2011, 3 pages.

Otagiri, M. et al. (1999). "Improving the Pharmacokinetic and Pharmacodynamic Properties of a Drug by Chemical Conversion to a Chimera Drug," *J. Control. Release* 62(1-2):223-229.

Poste, G. et al. (1976). "Lipid Vesicles as Carriers for Introducing Biologically Active Materials into Cells," Chapter 4 in *Methods in Cell Biology*, Prescott, D.M. ed., Academic Press, Inc.: New York, NY, XIV:33-71.

Prescott, L.F. et al. (1981). "Effects of Microsomal Enzyme Induction on Paracetamol Metabolism in Man," *British Journal of Clinical Pharmacology* 12:149-153.

Price, V.F. et al. (1982). "Increased Resistance of Diabetic Rats to Acetaminophen-Induced Hepatotoxicity," *Journal of Pharmacology and Experimental Therapeutics* 220(3):504-513.

Pu, Y. et al. (1991). "Synthesis and Acylation of Salts of L -Threonine β-Lactone: A Route to β-Lactone Antibiotics," *J. Org. Chem.* 56(3):1280-1283.

Raheja, K.L. et al. (1985). "Failure of Exogenous Prostaglandin to Afford Complete Protection Against Acetaminophen-Induced Hepatotoxicity in the Rat," *Journal of Toxicology and Environmental Health* 15:477-484.

Saha, S.K. et al. (Feb. 7, 1998). "Adding Methionine to Every Paracetamol Tablet," *BMJ* 316:473-474.

Savides, M.C. et al. (Jul. 1985). "Effects of Various Antidotal Treatments on Acetaminophen Toxicosis and Biotransformation in Cats," *American Journal of Veterinary Research* 46(7):1485-1489.

Skoglund, L.A. et al. (1984). "Comparison of a Traditional Paracetamol Medication and a New Paracetamol/Paracetamol-Methionine Ester Combination," *Eur. J. Clin. Pharmacol.* 26(5):573-577.

Skoglund, L.A. et al. (Sep. 15, 1986). "Efficacy of Paracetamol-Esterified Methionine Versus Cysteine or Methionine on

(56) References Cited

OTHER PUBLICATIONS

Paracetamol-Induced Hepatic GSH Depletion and Plasma ALAT Level in Mice," *Biochemical Pharmacology* 35(18):3071-3075.

Skoglund, L.A. et al. (1988). "In Vivo Studies on Toxic Effects of Concurrent Administration of Paracetamol and Its N-Acetyl-DL-Methionine Ester (SUR 2647 Combination)," *General Pharmacology* 19(2):213-217.

Skoglund, L.A. et al. (Mar. 1992). "Plasma Concentration of Paracetamol and Its Major Metabolites After p.o. Dosing with Paracetamol or Concurrent Administration of Paracetamol and Its N-Acetyl-DL-Methionine Ester in Mice," *General Pharmacology* 23(2):155-158.

Spiler, N.M. et al. (2005). "An Old Drug with a New Purpose: Cardiovascular Actions of Acetaminophen (Paracetamol)," *Curr. Drug Targets Cardiovasc. Haematol. Disord.* 5(5):419-429.

Thomas, B.H. et al. (1975). "Metabolism $^{14}$C-Ring-Labelled Paracetamol in Humans," *Biochemical Society Transactions* 3(5):687-688.

Thomas, B.H. et al. (1980). "Effect of Analgesic Nephropathy in Women on the Metabolism and Execration of $^{14}$C-Acetaminophen," *International Journal of Clinical Pharmacology, Therapy and Toxicology* 18(1):26-30.

Tredger, J.M. et al. (1985). "Effects of Ethanol Ingestion on the Hepatotoxicity and Metabolism of Paracetamol in Mice," *Toxicology* 36(4):341-352.

U.S. Appl. No. 12/993,088, filed May 20, 2009, for Muhammad et al.

U.S. Appl. No. 12/993,089, filed May 20, 2009, for Muhammad et al.

Wang, S-T. et al. (1997). "Methionine and Cysteine Affect Glutathione-Level, Glutathione-Related Enzyme Activities and the Expression of Glutathione S-Transferase Isozymes in Rat Hepatocytes," *Journal of Nutrition* 127:2135-2141.

Watkins, P.B. et al. (Jul. 5, 2006). "Aminotransferase Elevations in Healthy Adults Receiving 4 Grams of Acetaminophen Daily," *Journal Amer. Med. Assoc.* 296(1):87-93.

Whitehouse, L.W. et al. (May 1975). "Effect of Aspirin on Fate of $^{14}$C-Acetaminophen in Guinea Pigs," *Journal of Pharmaceutical Sciences* 64(5):819-821.

Williams, R.M. et al. (1991). "Asymmetric Synthesis of Monosubstituted and α, α-Disubstituted α-Amino Acids via Diastereoselective Glycine Enolate Alyklations," *J. Amer. Chem. Soc.* 113(24):9276-9286.

Williamson, J.M. et al. (Oct. 1982). "Intracellular Cysteine Delivery System that Protects Against Toxicity by Promoting Glutathione Synthesis," *Proc. Natl. Acad. Sci. USA* 79:6246-6249.

Wong, L.T. et al. (1976). "Metabolism of [$^{14}$C]Paracetamol and Its Interactions with Aspirin in Hamsters," *Xenobiotica* 6(9):575-584.

Written Opinion of the International Searching Authority dated Jul. 21, 2009, for PCT Patent Application No. PCT/US09/44749, filed on May 20, 2009, 6 pages.

\* cited by examiner

HEPATOPROTECTANT ACETAMINOPHEN MUTUAL PRODRUGS

CROSS REFERENCE TO RELATED APPLICATIONS

This application is a Continuation of U.S. patent application Ser. No. 12/993,091, which is a U.S. national phase application of PCT/US2009/044749 and has an International Filing Date of May 20, 2009, and which claims priority benefit of U.S. Provisional Application No. 61/054,777, entitled "Hepatoprotectant Acetaminophen Mutual Prodrugs" filed May 20, 2008, the contents of each of which are hereby incorporated by reference in their entirety as if they were set forth in full below.

BACKGROUND OF THE INVENTION

Acetaminophen (also known as paracetamol, and chemically known as N-(4-hydroxyphenyl)acetamide)) is a widely-used analgesic for the treatment of a variety of conditions related to pain. For example, acetaminophen is used to manage pain from surgery or traumatic injury, and pain produced by chronic inflammatory conditions such as osteoarthritis, rheumatoid arthritis, and lower back pain. In some cases acetaminophen is used to treat pain from mixed nociceptive/neuropathic etiologies, such as cancer or fibromyalgia. Acetaminophen also may have utility in management of other conditions, such as myocardial injury (Spiler N M, Rork T H, Merrill G F; *Curr Drug Targets Cardiovasc Haematol Disord.* 2005; 5(5):419-29) and nerve injury (Bisaglia M, Venezia V. Piccioli P, Stanzione S, Porcile C, Russo C, Mancini F, Milanese C, Schettini G. *Neurochem* 2002; 41(1):43-54).

Large quantities of acetaminophen (alone or in combination with other therapeutic agents, such as opioids) are manufactured, prescribed, and distributed throughout the world. With increasing concerns about the cardiovascular and gastrointestinal safety of conventional NSAIDs (such as ibuprofen and naproxen) and selective cyclooxygenase-2 inhibitors such as Vioxx®), patients and physicians have turned to acetaminophen for its seemingly lower safety risks.

However, it is well known that under certain conditions acetaminophen may be toxic to the liver (known as hepatotoxicity). It is estimated that most liver transplants in the United States are caused by acetaminophen toxicity, and 49% of all acute liver failure cases in 2004 were the result of acetaminophen overdose. Each year, overdoses of acetaminophen (sold as Tylenol® and other brands) account for more than 56,000 emergency room visits and an estimated 458 deaths from acute liver failure (Harvard Women's Health Watch, March, 2006). According to a recent study from the U.S. Acute Liver Failure Study Group (Lee W M. *Hepatology* 2004; 40(1):6-9), acetaminophen-related liver failure appears to be on the rise. Researchers at the University of Washington Medical Center in Seattle found that between 1998 and 2003, the percentage of acute liver failure cases attributed to acetaminophen nearly doubled, rising from 28% to 51%, Acetaminophen toxicity may go beyond liver and may involve kidneys and/or myocardium (J T DiPiro, R L Talbert, G C Yee, G R Matzke, B G Wells, L M Posey (eds) Pharmacotherapy: A Physiological Approach 6$^{th}$ ed McGraw Hill (New York 2005) pp. 133).

Acetaminophen's daily dose limit of 4 grams reduces its therapeutic utility as 4 grains can be consumed in 16 hours (1 gram every 4 hours) leaving the remaining 8 hours of the day to seek alternative analgesics. Further, ethnic and inter-subject variability in acetaminophen metabolism have been reported to be as high as 60-fold (S. Bridger, et al. BMJ 1998; 316:1724-1725), which complicates the acetaminophen safety profile as it imparts a high degree of uncertainty in the toxic dose for a given patient. By attenuating toxicity, improved compounds may provide greater utility by allowing doses higher than 4 grams and/or provide a larger safety margin for patients of any ethnic background.

Acetaminophen induced hepatic toxicity has been found to be dependent on both acetaminophen blood level concentration and length of exposure. Consequently, acetaminophen package labels instruct patients to not use the maximum dosage (4000 mg per day) for more than 10 days, and to not take the product for pain for more than 10 days, or for fever for more than 3 days unless directed by a physician. Even healthy adults receiving 4000 mg of acetaminophen per day for 14 days show elevated levels of enzymes indicative of liver toxicity (*Journal Amer. Med. Assoc.* 296, 87-93, 2006).

It is known that after administration, about 90% of acetaminophen is conjugated with glucuronide and sulphate, and less than 5% remains unmetabolized. The remaining ~5% of acetaminophen is metabolized in the liver by cytochrome P450 mixed-function oxygenase system (mainly by CYP2E1), and is converted to N-acetyl-p-benzquinone imine (NAPQI) (J T DiPiro, R L Talbert, G C Yee, G R Matzke, B G Wells, L M Posey (eds) Pharmacotherapy: A Physiological Approach 6$^{th}$ ed McGraw Hill (New York 2005) pp. 133). NAPQI is capable of damaging proteins by covalently binding to nucleophilic residues (e.g., cysteine residues). Glutathione (GSH; a tripeptide of L-glutamate, L-cysteine and L-glycine) aids in detoxification by conjugating with NAPQI and may be depleted by as much as 90% following a toxic dose of acetaminophen. Low concentrations of GSH in centrilobular cells of liver can lead to centrilobular hepatic necrosis, which can be fatal (*Drug Metabolism and Disposition* 31: 1499-1506, 2003). The GSH adduct with NAPQI is either excreted into bile or further metabolized via the mercapturic acid pathway, which involves removal of glutamyl and glycine groups and conversion of cysteine to N-acetylcysteine conjugate. (*The Journal of Pharmacology and Experimental Therapeutics* 294: 735-745, 2000).

N-acetylcysteine (NAC) also called acetylcysteine (Acetadote®) is an FDA-approved antidote for acetaminophen toxicity available in both oral as well as intravenous dosage form. (Acetadote® package insert. Cumberland Pharmaceuticals, Nashville, Tenn. Issued March 2004.) NAC has been known to prevent or mitigate hepatic toxicity of acetaminophen by stimulating glutathione synthesis (by promoting metabolic pathways) which produces nontoxic metabolites of acetaminophen and/or by detoxifying toxic metabolites (In *Goldfrank's Toxicologic Emergencies* 7$^{th}$ Ed. New York: McGraw-Hill; 2002, 502-506). However, NAC only has been shown to be effective at minimizing hepatic toxicity when administered within 8-10 hours of acute exposure to toxic blood levels of acetaminophen. Anaphylactoid reactions to intravenously administered NAC have also been reported (Lynch R M, Robertson R. *Accid Emerg Nurs.* 2004; 12(1):10-5).

Cysteine and methionine (methionine can be converted to cysteine through the hepatic cystathionine pathway) can ensure the maintenance of normal hepatic GSH levels when supplied in adequate amounts. GSH can also be a transport and storage form of cysteine (*Journal of Nutrition,* 127: 2135-2141, 1997). Extracellular methionine has found to be as strong an antioxidant as cysteine against intracellular reactive oxygen species (*Metabolic Bases of Inherited Disease* 5th Ed, New York: McGraw-Hill; 1982, 522-559). Oral administration of methionine has been used to treat acetaminophen overdoses, as 30 patients at risk of hepatic damage from acetaminophen ingestion were given 2-5 g oral methionine every four hours up to a total dose of 10 g; where the first dose was given within ten hours of the overdose. There were no deaths and no reports of hepatic encephalopathy or other complications following administration of the methionine (Crome P, Vale J A, Volans G N, Widdop B, Goulding R. *Lancet.* 1976; 2(7990):829-30). A combination of acetaminophen (500 mg) and methionine (100 mg) is available in the United Kingdom (Paradote®) to prevent the onset of acetaminophen poisoning through the maintenance of high glutathione levels in the liver. The methionine in this formulation contains both the L-isomer (an essential amino acid in humans) and the D-isomer (unnatural). Cysteine and acetylmethionine coupled to acetaminophen have been described in DE 4327462A1 and Skoglund L A, Skjelbred P. *Eur J Clin Pharmacol* 1984; 26(5):573-7.

Administration of procysteine (L-2-oxothiazolidine-4-carboxylate), which is converted to L-cysteine by 5-oxo-L-prolinase, may result in an increase of intracellular cysteine levels and has been shown to increase GSH synthesis. This effect has been shown to be more pronounced when administered prior to acetaminophen than when administered after acetaminophen (e.g., administration of L-2-oxothiazolidine-4-carboxylate 30 minutes post-acetaminophen administration caused GSH tissue levels to reach 6.1 µmol/g, of tissue compared to 5.3 µmol/g of tissue when administered 120 minutes post-acetaminophen administration; *Proceedings of The Natural Academy of Sciences,* 79: 6246-6249, 1982).

Some patients (e.g., those with chronic pain) may seek acetaminophen treatment for extended periods to avoid the potentially adverse events of alternative analgesics, such as NSAIDs, selective COX-2 inhibitors, and opioids. Additionally, patients with higher risks for hepatotoxicity (e.g., those with pre-existing liver damage and/or other stressors on the liver, such as alcohol consumption), may still benefit by having access to acetaminophen to control pain and fever.

Accordingly, it would be desirable to provide improved formulations or prodrugs of acetaminophen which address the important problem of hepatotoxicity while maintaining its therapeutic properties and/or which could alter the physicochemical properties of the acetaminophen to allow the development of alternative dosage forms.

The disclosures of all publications, patents, patent applications and other references referred to herein are hereby incorporated herein by reference in their entireties.

BRIEF SUMMARY OF THE INVENTION

One aspect of the invention provides a compound comprising an acetaminophen moiety and a hepatoprotectant moiety; or a pharmaceutically acceptable salt thereof or solvate of the foregoing.

In some embodiments, the invention embraces a compound comprising an acetaminophen moiety and a hepatoprotectant moiety, wherein the hepatoprotectant moiety is capable of inactivating N-acetyl-p-benzoquinone imine (NAPQI).

In some embodiments, the invention embraces a compound comprising an acetaminophen moiety and a hepatoprotectant moiety, wherein the compound is capable of sufficiently inactivating N-acetyl-p-benzoquinone imine (NAPQI) in an individual relative to a molar equivalent of acetaminophen administered under the same conditions.

In some embodiments, the invention embraces a compound comprising an acetaminophen moiety and a hepatoprotectant moiety, wherein the compound is capable of sufficiently decreasing liver damage in an individual relative to a molar equivalent of acetaminophen administered under the same conditions.

In some embodiments, the invention embraces a compound comprising an acetaminophen moiety and a hepatoprotectant moiety, wherein the compound is capable of sufficiently decreasing kidney damage (e.g., renal toxicity) in an individual relative to a molar equivalent of acetaminophen administered under the same conditions.

In some embodiments, the invention embraces a compound comprising an acetaminophen moiety and a hepatoprotectant moiety, wherein the hepatoprotectant moiety is capable of stimulating glutathione synthesis.

In another aspect, the present invention provides a compound of formula (I):

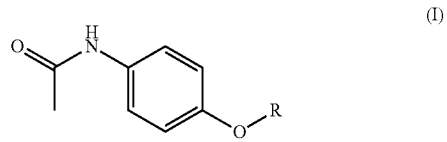

wherein R is a hepatoprotectant moiety, or a pharmaceutically acceptable salt thereof or solvate of the foregoing. In some embodiments, the compound of formula (I) is other than 4-acetamidophenyl 2-acetamido-4-(methylthio)butanoate; 4-acetamidophenyl 2-acetamido-3-mercaptopropanoate; or 4-acetamidophenyl 2-amino-3-mercaptopropanoate.

In another aspect, the present invention provides a compound of formula (II):

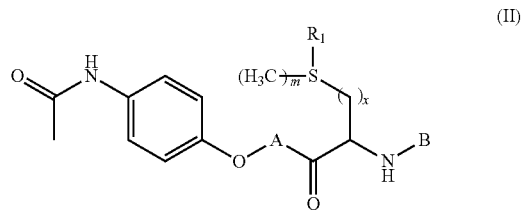

wherein A is a bond or a substituted or unsubstituted amino acid moiety; B is —H, acetyl, or a substituted or unsubstituted amino acid moiety; $R_1$ is —H, —$CH_3$, an alkylenephosphate moiety, a substituted or unsubstituted amino acid moiety, or a substituted or unsubstituted nucleoside moiety; or wherein B is taken together with $R_1$ to form a substituted or unsubstituted heterocycloalkyl; x is 1 or 2; and no is 0 or 1; or a pharmaceutically acceptable salt thereof or solvate of the foregoing. In some embodiments, when A is a bond, and $R_1$ is methyl or —H, B is a substituted or unsubstituted amino acid moiety; or a pharmaceutically acceptable salt thereof or solvate of the foregoing.

In some embodiments, the compound of formula (II) is 4-acetamidophenyl 2-amino-4-(methylthio)butanoate; 2-acetamido-3-((2-acetamido-3-(4-acetamidophenoxy)-3-oxopropyl)disulfanyl)propanoic acid; 3-((2-acetamido-3-(4-acetamidophenoxy)-3-oxopropyl)disulfanyl)-2-aminopropanoic acid; 2-acetamido-3-((3-(4-acetamidophenoxy)-2- amino-3-oxopropyl)disulfanyl)propanoic acid; 3-((3-(4-acetamidophenoxy)-2-amino-3-oxopropyl)disulfanyl)-2-aminopropanoic acid; 5-(1-(2-(4-acetamidophenoxy)-2-oxoethylamino)-3-mercapto-1-oxopropan-2-ylamino)-2-amino-5-oxopentanoic acid; 4-acetamidophenyl 2-oxothiazolidine-4-carboxylate; 4-acetamidophenyl 2-acetamido-3-(phosphonooxymethylthio)propanoate; (4-(4-acetamidophenoxy)-3-amino-4-oxobutyl)((5 (6 amino-9H-purin-9-yl)-3,4-dihydroxytetrahydrofuran-2 yl)methyl)(methyl)sulfonium; 4-acetamidophenyl 2-acetamido-4-(methylthio)butanoate; 4-acetamidophenyl 2-acetamido-3-mercaptopropanoate; 4-acetamidophenyl 2-acetamido-3-(methylthio)propanoate; or a pharmaceutically acceptable salt thereof or solvate of the foregoing.

In another aspect, the present invention provides a compound of formula (III):

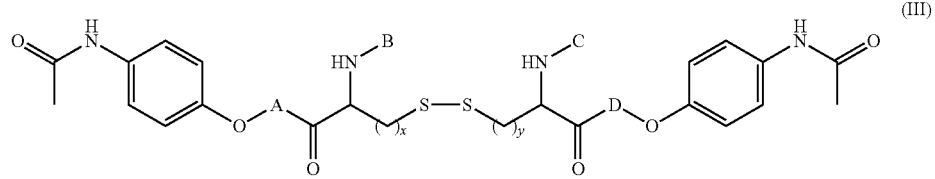

wherein A and D are each independently a bond or a substituted or unsubstituted amino acid moiety; B and C are each independently —H, acetyl, or a substituted or unsubstituted amino acid moiety; and x and y are each independently 1 or 2; or a pharmaceutically acceptable salt thereof or solvate of the foregoing. In some embodiments of the compound of formula (III), when A and D are each a bond; x and y are each 1; and B is acetyl, then C is —H, or a substituted or unsubstituted amino acid moiety.

In some embodiments, the compound of formula (III) is bis(4-acetamidophenyl) 3,3'-disulfanediylbis(2-aminopropanoate); 4-acetamidophenyl 2-acetamido-3-((3-(4-acetamidophenoxy)-2-amino-3-oxopropyl)disulfanyl)propanoate; 5,5'-(3,3'-disulfanediylbis(1-(2-(4-acetamidophenoxy)-2-oxoethylamino)-1-oxopropane-3,2-diyl))bis(azanediyl)bis(2-amino-5-oxopentanoic acid); or a pharmaceutically acceptable salt thereof or solvate of the foregoing. In some embodiments, the compound of formula (III) is other than bis(4-acetamidophenyl) 3,3'-disulfanediylbis(2-acetamidopropanoate).

In some embodiments, the invention embraces a formulation comprising a compound of any one of formulas I, II, or III, a pharmaceutically acceptable salt thereof or solvate of the foregoing, and a carrier. In some embodiments, the formulation comprises an effective amount of a compound of any one of formulas I, II, or III, or a pharmaceutically acceptable salt thereof or solvate of the foregoing, and a carrier. In some embodiments, the carrier is a pharmaceutically acceptable carrier. In some embodiments, the invention embraces a substantially pure form of a compound of any one of formulas I, II or III, or a pharmaceutically acceptable salt thereof or solvate of the foregoing.

In some embodiments, the invention embraces a formulation comprising the compound of any one of formulas I, II, or III, or a pharmaceutically acceptable salt thereof or solvate of the foregoing, and an opioid, a non-steroidal anti-inflammatory drug (NSAID), a benzodiazepine, and/or a barbiturate. In some embodiments, the invention embraces a formulation comprising the compound of any one of formulas I, II, or III, or a pharmaceutically acceptable salt thereof or solvate of the foregoing, and codeine, morphine, hydrocodone, hydromorphone, levorphanol, propoxyphene, aspirin, ketorolac, ibuprofen, ketoprofen, flurbiprofen, etodolac, diclofenac, misoprostol, meloxicam, piroxicam, naproxen, caffeine, doxylamine, pamabrom, tramadol, dextropropoxyphene, methylhexital, carisoprodol, butalbital, diazepam, lorazepam, and/or midazolam.

In another aspect, the present invention provides methods of treating a disease or condition that is responsive to acetaminophen (e.g., pain, fever, inflammation, ischemic injury (such as myocardial and/or cerebral), neuronal injury, etc.) comprising administering to an individual an effective amount of the compound of any one of formulas I, II or III or a pharmaceutically acceptable salt thereof or solvate of the foregoing. In some embodiments, the potential hepatotoxicity of acetaminophen following administration of the compound is reduced relative administration of acetaminophen under the same conditions. In some of these embodiments, the hepatotoxicity comprises damage to the liver and/or damage to the kidneys of the individual. In some embodiments, the amount of inactivated N-acetyl-p-benzoquinone imine (NAPQI) in an individual following administration of the compound is increased relative to administration of acetaminophen under the same conditions. In some embodiments, the hepatoprotectant moiety of the compound stimulates glutathione synthesis.

In some embodiments of the methods, the compound of any one of formulas I, II or III is administered orally. In some embodiments, the compound is administered parenterally (e.g., intravenously or intramuscularly). In some embodiments, the compound is administered in a dosage of about 300 mg to about 3.6 g, or about 750 mg to about 3.6 g. In some embodiments, the compound is administered in a dosage of about 1 μmol to about 10 mmol. In some embodiments, the compound is administered in a dosage of about 10 μmol/kg to about 100 μmol/kg.

In another aspect, the present invention provides methods of delaying the onset of acetaminophen action in an individual, the method comprising administering to the individual an effective amount of a compound of any one of formulas I, II or III wherein the compound provides a slower onset of acetaminophen action as compared to acetaminophen. In another aspect, the present invention provides methods of delaying the onset of hepatoprotectant action in an individual, the method comprising administering to the individual an effective amount of a compound of any one of formulas I, II or III wherein the compound provides a slower onset of hepatoprotectant action as compared to the hepatoprotectant of the compound.

In another aspect, the present invention provides methods of prolonging acetaminophen activity in an individual, the method comprising administering to the individual an effective amount of a compound of any one of formulas I, II or III wherein the compound provides prolonged acetaminophen activity as compared to acetaminophen. In another aspect, the present invention provides methods of prolonging hepatoprotectant activity in an individual, the method comprising administering to the individual an effective amount of a compound of any one of formulas I, II or III wherein the compound provides prolonged hepatoprotectant activity as compared to the hepatoprotectant of the compound.

In another aspect, methods of administering low volume/high concentration formulations are provided where the formulations comprise a compound of any one of formulas I, II or III and wherein the compound exhibits enhanced solubility (e.g., water solubility) as compared to the solubility of the acetaminophen. Low volume/high concentration formulations are also provided herein, such as formulations comprising a compound of any one of formulas I, II or III and a pharmaceutically acceptable carrier. A "low volume/high concentration" formulation intends a formulation comprising a carrier and prodrug where a given volume of carrier contains a higher molar concentration of prodrug than is available or obtainable using acetaminophen. Taking the compound of formula (II-A) as an example, a low volume/high concentration of such prodrug intends a formulation comprising a carrier and the prodrug wherein the formulation contains a higher molar concentration of prodrug in a given volume of carrier than is available or obtainable using acetaminophen. Methods of providing low volume/high concentrations of acetaminophen are also provided comprising administering to an individual a low volume/high concentration formulation of a prodrug as detailed herein (e.g., a prodrug of a compound of any one of formulas I, II or III or a salt thereof or solvate of the foregoing). In one aspect, the methods entail administering a prodrug that results in rapid release of acetaminophen and a hepatoprotectant when administered to an individual (e.g., by enzymatic cleavage or hydrolysis). Also provided are methods of providing a single dose of acetaminophen in an amount that exceeds currently available doses by administering a prodrug as detailed herein.

In another aspect is provided the use of a compound of any one of formulas I, II, or III or a pharmaceutically acceptable salt thereof or solvate of the foregoing for the manufacture of a medicament for the treatment of a condition responsive to acetaminophen. In another aspect is provided the use of a compound of any one of formulas I, II, or III or a pharmaceutically acceptable salt thereof or solvate of the foregoing for the treatment of a condition responsive to acetaminophen. In some variations, the condition is pain, fever, inflammation, ischemic injury, or neuronal injury.

In another aspect, the present invention provides a kit comprising a compound of any one of formulas I, II or III or a pharmaceutically acceptable salt thereof or solvate of the foregoing, and instructions for use. In some embodiments, the instructions relate to the use of a compound of any one of formulas I, II or III for the treatment or prevention of a disease or condition that is responsive to acetaminophen (e.g., pain, fever, inflammation, ischemic injury (such as myocardial and/or cerebral), or neuronal injury).

In another aspect, the present invention provides a kit comprising a formulation of a compound of any one of formulas I, II or III and instructions for use. In some embodiment, the instructions relate to the use of a compound of any one of formulas I, II or III for the treatment or prevention of a disease or condition that is responsive to acetaminophen (e.g., pain, fever, inflammation, ischemic injury (such as myocardial and/or cerebral), or neuronal injury).

DETAILED DESCRIPTION OF THE INVENTION

Figure 1:
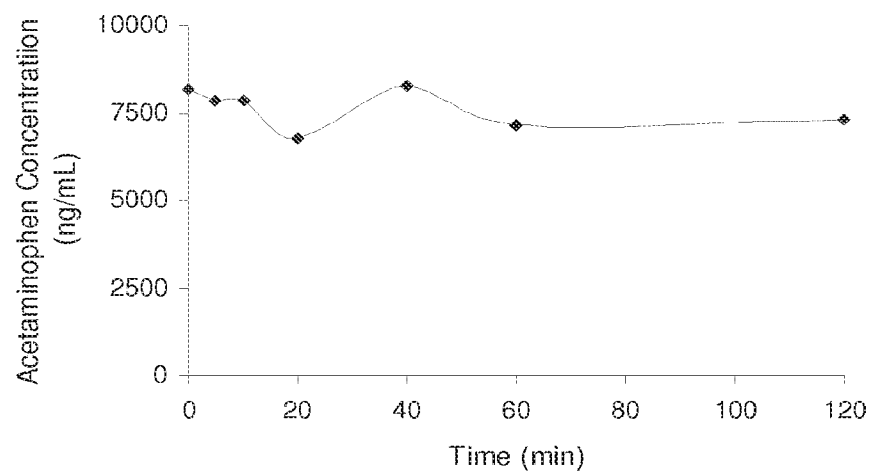
FIG. 1 shows the formation of acetaminophen from 1.5 µg/mL of compound (II-A) in human plasma.

The present invention provides hepatoprotectant acetaminophen mutual prodrugs which have an acetaminophen moiety covalently linked to a second moiety that may act as a hepatoprotectant against acetaminophen toxicity. These compounds may consist of two biologically active compounds coupled together, such that the two compounds may be released following administration and metabolism (Otagiri M, Imai T, Fukuhara A. *J Control Release.* 1999; 62(1-2):223-9). Accordingly, these compounds may provide acetaminophen and a hepatoprotectant in vivo and may provide improved safety profiles and/or water solubility compared to administration of acetaminophen alone. Such compounds may be particularly useful for high dosage and/or prolonged treatment of conditions responsive to acetaminophen (e.g., pain, fever, inflammation, ischemic injury (such as myocardial and/or cerebral), or neuronal injury).

Accordingly, the present invention in one aspect provides a compound comprising an acetaminophen moiety and a hepatoprotectant moiety, or a pharmaceutically acceptable salt thereof or solvate of the foregoing.

In another aspect, the present invention provides methods of treating a disease or condition that is responsive to acetaminophen (e.g., pain, fever, inflammation, ischemic injury (such as myocardial and/or cerebral), or neuronal injury, etc.) using the hepatoprotectant acetaminophen mutual prodrugs described herein.

Also provided are kits, formulations and unit dosage forms of the hepatoprotectant acetaminophen mutual prodrugs.

Abbreviations and Definitions

Nomenclature of some compounds described herein may be identified using ChemDraw Ultra Version 10.0, available from CambridgeSoft®.

As used herein, the term "acetaminophen moiety" refers to a substituted or unsubstituted radical of N-(4-hydroxyphenyl)acetamide. Compounds comprising an acetaminophen moiety include, but are not limited to, N-(4-propoxyphenyl)acetamide, 2-acetamido-3-((2-acetamido-3-(4-acetamidophenoxy)-3-oxopropyl)disulfanyl)propanoic acid, N-(3-ethyl-4-isopropoxyphenyl)acetamide, 2-fluoro-N-(4-hydroxyphenyl)acetamide, (S)-4-acetamidophenyl 2-amino-4-(methylthio)butanoate, and 6-acetamido-3-hydroxy-2-methylphenyl acetate.

As used herein, "hepatotoxicity" refers to one or more adverse effect(s) of acetaminophen on one or more organs (e.g., liver and/or kidney) in an individual. Assessment of hepatotoxicity includes, but is not limited to, evaluations of signs and symptoms associated with side-effects of acetaminophen as known to those skilled in art. Laboratory tests, for example, may include a determination and/or quantification of alanine aminotransferase (ALT), aspartate aminotransferase (AST), serum bilirubin, international normalization ratio (INR), serum creatinine, blood urea nitrogen, acetaminophen blood levels, and blood levels of acetaminophen conjugates. In some cases, ultrasound may used to assess hepatomegaly. Non-limiting examples of effects of hepatotoxicity include acute liver failure, hepatorenal renal syndrome, and/or myocardial injury.

As used herein, "hepatoprotectant" refers to a compound that is effective at treating hepatotoxicity in an individual, which may include decreasing the onset and/or severity of one or more symptoms known or believed to be associated with hepatotoxicity. A hepatoprotectant may be a compound, or capable of forming a compound in situ, which stimulates glutathione synthesis and/or is capable of inactivating N-acetyl-p-benzoquinone imine (NAPQI) under physiological conditions. Non-limiting examples of hepatoprotectants include glutathione and N-acetyl-cysteine. A "hepatoprotectant moiety" is a radical of a hepatoprotectant compound.

The term "prodrug" refers to a compound which provides an active compound following administration to the individual in which it is used, by a chemical and/or biological process in vivo (e.g., by hydrolysis and/or an enzymatic conversion). The prodrug itself may be active, or it may be relatively inactive, then transformed into a more active compound. The invention embraces prodrugs of acetaminophen and hepatoprotectants, as described herein.

As used herein, "delaying the onset" or "delayed onset" refers to the increased time to onset of action provided by a hepatoprotectant acetaminophen mutual prodrug as compared to administration of the molar equivalent of acetaminophen and/or a hepatoprotectant within the same time period through the same route of administration. For example, the delayed release of acetaminophen and/or a hepatoprotectant from the prodrug 4-acetamidophenyl 2-amino-4-(methylthio)butanoate may result in delayed systemic exposure to acetaminophen and/or the hepatoprotectant as compared to administration of the molar equivalent of acetaminophen and/or the hepatoprotectant to an individual.

As used herein, "prolonging activity" or "prolonged activity" refers to the sustained action provided by a hepatoprotectant acetaminophen mutual prodrug by virtue of the time required to release or otherwise generate acetaminophen and/or a hepatoprotectant from the prodrug. For example, administration of the prodrug (4-acetamidophenyl 2-amino-4-(methylthio)butanoate may result in sustained release of acetaminophen and/or a hepatoprotectant as compared to administration of the molar equivalent of acetaminophen and/or a hepatoprotectant over the same time period through the same route of administration. "Sustained release" refers to release of the acetaminophen and/or a hepatoprotectant, at a rate such that the blood concentration of the acetaminophen and/or hepatoprotectant (or metabolite thereof) in an individual is maintained at or within the therapeutic range (e.g., above the minimum effective analgesic concentration but below toxic levels) for an extended duration. The extended duration in this context intends any time greater than the time that the molar equivalent of corresponding acetaminophen and/or a hepatoprotectant, administered through the same route, results in an acetaminophen and/or a hepatoprotectant (or metabolite thereof) blood concentration within the therapeutic range.

The term "alkyl," by itself or as part of another substituent, means, unless otherwise stated, a fully saturated straight-chain (linear; unbranched) or branched chain, or combination thereof, having the number of carbon atoms specified, if designated (i.e. $C_1$-$C_{10}$ means one to ten carbons). Examples include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. If no size is designated, the alkyl groups mentioned herein contain 1-20 carbon atoms, typically 1-10 carbon atoms, or 1-8 carbon atoms, or 1-6 carbon atoms, or 1-4 carbon atoms. The term "alkylene" is by itself or in combination with other terms, represents a divalent radical derived from an alkyl, as exemplified, but not limited, by —$CH_2CH_2CH_2$—. In some embodiments, the alkylene group is methylene or ethylene.

The term "heterocycloalkyl," by itself or in combination with other terms, represents a saturated or unsaturated cyclic hydrocarbon radical containing of at least one carbon atom and at least one annular heteroatom selected from the group consisting of O, N, P, Si and S, and wherein the nitrogen and sulfur atoms may optionally be oxidized and the nitrogen heteroatom may optionally be quaternized. The heteroatom(s) O, N, P, S and Si may be placed at any interior position of the heterocycloalkyl group or at the position at which the heterocycloalkyl group is attached to the remainder of the molecule. Examples of heterocycloalkyl include, but are not limited to, thiazolidinonyl, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "amino acid" as used herein refers to any of the naturally occurring amino acids, as well as synthetic analogs (e.g., D-stereoisomers of the naturally occurring amino acids, such as D-methionine) and derivatives thereof. Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). Unnatural amino acids are also known in the art, as set forth in, for example, Williams (ed.), Synthesis of Optically Active a-Amino Acids, Pergamon Press (1989); Evans et al., J. Amer. Chem. Soc., 112:4011-4030 (1990); Pu et al., J. Amer. Chem. Soc., 56:1280-1283 (1991); Williams et al., J. Amer. Chem. Soc., 113:9276-9286 (1991); and all references cited therein. The present invention includes the side chains of unnatural amino acids as well.

The term "nucleoside" as used herein refers to a compound comprising a purine or pyrimidine base, or derivative thereof, linked to a ribose, deoxyribose, dideoxyribose, or similar moiety. Nucleosides include any of the naturally occurring nucleosides (e.g., adenosine, cytidine, uridine, guanosine, thymidine, and the like), as well as synthetic analogs. The present invention includes both D and L enantiomers.

"Protecting group" refers to a chemical group that exhibits the following characteristics: 1) is stable to the projected reactions for which protection is desired; 2) is removable from the protected substrate to yield the desired functionality; and 3) is removable by reagents compatible with the other functional group(s) present or generated in such projected reactions. Selection of suitable protecting groups for use in the methods described herein is within the ordinary skill level in the art. Examples of suitable protecting groups can be found in Greene et al. (2006) PROTECTIVE GROUPS IN ORGANIC SYNTHESIS, 4th Ed, (John Wiley & Sons, Inc., New York). A "hydroxy protecting group" as used herein denotes a group capable of protecting a free hydroxy group to generate a "protected hydroxyl" which, subsequent to the reaction for which protection is employed, may be removed without disturbing the remainder of the compound. Exemplary hydroxy protecting groups include, hut are not limited to, ethers (e.g., allyl, triphenylmethyl (trityl or Tr), benzyl, p-methoxybenzyl (PMB), p-methoxyphenyl (PMP)), acetals (e.g., methoxymethyl (MOM), 3-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TI PS), triphenylsilyl (TPS), tert-butyldimethylsilyl (TBDMS), tert-butyldiphenylsilyt (TBDPS) and the like.

As used herein, "treatment", "treating", or "treat" is an approach for obtaining beneficial or desired results, including clinical results. For purposes of this invention, beneficial or desired, results include, but are not limited to, one or more of the following: decreasing one or more symptoms of hepatotoxicity and/or a disease or condition that is responsive to acetaminophen, diminishing the extent of hepatotoxicity and/or the disease or condition that is responsive to acetaminophen, stabilizing hepatotoxicity and/or the disease or condition that is responsive to acetaminophen (e.g., preventing or delaying the worsening of hepatotoxicity and/or the disease or condition), delaying or slowing the progression of hepatotoxicity and/or the disease or condition that is responsive to acetaminophen, ameliorating hepatotoxicity and/or the disease or condition that is responsive to acetaminophen, decreasing the dose of one or more other medications required to treat hepatotoxicity and/or the disease or condition that is responsive to acetaminophen, and increasing the quality of life of an individual who has been or is suspected of having hepatotoxicity and/or a disease or condition that is responsive to acetaminophen. The disease or condition may be one that is or is believed to be responsive to acetaminophen (e.g., a disease or condition that is accompanied by a fever and/or pain). The disease or condition may be accompanied by inflammation. The disease or condition may be ischemic injury. The disease or condition may be a neuronal injury. In one variation the condition is post-surgical pain and/or fever. In some embodiments, the hepatoprotectant acetaminophen mutual prodrug and/or formulation comprising the prodrug reduces the severity of one or more symptoms associated with hepatotoxicity and/or the disease or condition that is responsive to acetaminophen by at least about any of 10%, 20%, 30%, 40%, 50%, 60%, 70%, 80%, 90%, 95%, or 100% compared to the corresponding symptom in the same subject prior to treatment or compared to the corresponding symptom in other subjects not receiving the hepatoprotectant acetaminophen mutual prodrug and/or formulation. "Responsive to acetaminophen" as used herein refers to a disease or condition, and/or symptom of a disease or condition, which may be treated with acetaminophen. Commonly evaluated signs of hepatotoxicity include, for example, elevated blood levels of hepatic enzymes alanine aminotransferase (ALT), aspartate aminotransferase (AST) and gamma-glutamyltransferase (GGT) as determined in liver function tests (LFTs) by those skilled in art. Other signs include hepatic necrosis, hepatic inflammation (hepatitis) and hepatic steatosis and hepatomegaly. Exemplary symptoms of hepatotoxicity include anorexia, diarrhea, lethargy, jaundice, abdominal pain, nausea, and vomiting.

As used herein, "delaying" means to defer, hinder, slow, retard, stabilize, and/or postpone development of, and/or one or more symptoms of, hepatotoxicity and/or a disease or condition that is responsive to acetaminophen. This delay can be of varying lengths of time, depending on the history of the disease and/or individual being treated. As is evident to one skilled in the art, a sufficient or significant delay can, in effect, encompass prevention, in that the individual does not develop hepatotoxicity and/ova disease or condition that is responsive to acetaminophen. A method that "delays" development of hepatotoxicity and/or a disease or condition that is responsive to acetaminophen is a method that reduces the probability of hepatotoxicity development from acetaminophen and/or a development of a disease or condition that is responsive to acetaminophen in a given time frame and/or reduces the extent of hepatotoxicity and/or a disease or condition that is responsive to acetaminophen in a given time frame, when compared to not using the method. Such comparisons are typically based on clinical studies, using a statistically significant number of subjects.

As used herein, an "at risk" individual is an individual who is at risk of developing hepatotoxicity and/or a disease or condition that is responsive to acetaminophen (e.g., pain, fever, inflammation, ischemic injury (such as myocardial and/or cerebral), or neuronal injury). An individual "at risk" may or may not have detectable hepatotoxicity and/or a detectable disease or condition that is responsive to acetaminophen, and may or may not have displayed symptoms associated with detectable hepatotoxicity and/or a detectable disease or condition that is responsive to acetaminophen prior to the treatment methods described herein. "At risk" denotes that an individual has one or more so-called risk factors, which are measurable parameters that correlate with development of hepatotoxicity and/or a disease or condition that is responsive to acetaminophen. An individual having one or more of these risk factors has a higher probability of developing hepatotoxicity and/or a disease or condition that is responsive to acetaminophen than an individual without these risk factor(s).

As used herein, "pharmaceutically acceptable" refers to a material that is not biologically or otherwise undesirable, e.g., the material may be incorporated (e.g., at the time of manufacturing or administration) into a pharmaceutical composition administered to an individual without causing any significant undesirable biological effects or interacting in a deleterious manner with any of the other components of the composition in which it is contained. As used herein, the term "pharmaceutically acceptable carrier," refers to, for example, solvents, stabilizers, pH-modifiers, tonicity modifiers, adjuvants, binders, diluents, etc., known to the skilled artisan that are suitable for administration to an individual (e.g., a human). Combinations of two or more carriers are also contemplated in the present invention. The pharmaceutically acceptable carrier(s) and any additional components, as described herein, should be compatible for use in the intended route of administration (e.g., oral, parenteral) for a particular dosage form. Such suitability will be easily recognized by the skilled artisan, particularly in view of the teaching provided herein. Pharmaceutically acceptable carriers or excipients have preferably met the required standards of toxicological and manufacturing testing and/or are included on the Inactive Ingredient Guide prepared by the U.S. Food and Drug administration.

The term, "effective amount," as used herein refers to an amount that results in a desired pharmacological and/or physiological effect in an individual who has or is suspected of having (e.g., based on symptoms and/or an individual's perceptions/feelings) a disease or condition or who displays one or more of its symptoms. An effective amount may completely or partially prevent the occurrence or recurrence of the disease or condition or symptom thereof and/or may be therapeutic in terms of a partial or complete cure for the disease or condition and/or adverse effect attributable to the disease or condition (e.g., pain). In reference to a disease or condition described herein (e.g., pain), an effective amount may comprise an amount sufficient to, among other things, reduce and/or relieve to some extent one or more of the symptoms associated with a disease or condition that is responsive to acetaminophen (e.g., pain, fever, inflammation, ischemic injury (such as myocardial and/or cerebral), or neuronal injury). In certain embodiments, the effective amount is sufficient to prevent the condition, as in being administered to an individual prophylactically. Effective amount includes the eradication or amelioration of the underlying condition being treated and/or eradication or amelioration of one or more of the symptoms associated with the underlying condition such that the individual reports an improvement in feeling or condition (e.g., decreased pain intensity and/or duration), notwithstanding that the individual may still be afflicted with the underlying disease or condition. Effective amount also includes halting or slowing the progression of the disease or condition, regardless of whether improvement or the disease or condition is realized.

The "effective amount" may vary depending on the composition being administered, the condition being treated/prevented (e.g., the type of pain), the severity of the condition being treated or prevented, the age, body size, weight, and relative health of the individual, the route and form of administration, the judgment of the attending medical or veterinary practitioner (if applicable), and other factors appreciated by the skilled artisan in view of the teaching provided herein. An effective amount may be assessed, for example, by using data from one or more clinical, physiological, biochemical, histological, electrophysiological, and/or behavioral evaluations.

As is understood in the art, an "effective amount" may be in one or more doses, i.e., a single dose or multiple doses may be required to achieve the desired treatment endpoint. An effective amount may be considered in the context of administering one or more additional pharmaceutical agents, and a hepatoprotectant acetaminophen mutual prodrug may be considered to be given in an effective amount if, in conjunction with one or more additional pharmaceutical agents, one or more desirable or beneficial result(s) may be or are achieved.

When used with respect to methods of treatment and/or prevention and the use of the hepatoprotectant acetaminophen mutual prodrugs thereof described herein, an individual "in need thereof" may be an individual who has been diagnosed with, previously treated for, and/or suspected of having the disease or condition to be treated. With respect to prevention, the individual in need thereof may also be an individual who is at risk for a disease or condition (e.g., a family history of the condition, life-style factors indicative of risk for the condition, etc.). Individuals particularly higher risk of acetaminophen induced hepatotoxicity include, for example, those with deficient glutathione stores (e.g., alcoholics, patients with AIDS, anorexia nervosa and malnutrition) and those producing relatively higher levels of NAPQI due to enhanced activity of P450 oxidative enzyme system (particularly those isozymes involved in the metabolism of acetaminophen, i.e. cyp2E1, cyp1A2 and cyp3A4). These aforementioned enzymes may be induced in patients taking drugs such as isoniazid, aspirin, chlorzoxazone, clofibrate, ciprofibrate, omeprazole, tobacco, modafinil, nafcillin, phenytoin, carbamazepine, phenobarbital, rifampin, erythromycin, lovastatin, and/or prednisone.

In some variations, the individual has been identified as having one or more diseases or conditions, and/or symptoms thereof described herein. Identification of the diseases or conditions and/or symptoms thereof by a skilled physician is routine in the art (e.g., detection of allergies, cold, cough, flu, pain, etc.) and may also be suspected by the individual or others, for example, due to pain, fever, etc.

In some embodiments, the individual has been identified as susceptible to one or more of the diseases or conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions), lifestyle or habits.

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children, infants, and preemies. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. In some embodiments, the individual is a non-mammal, including, but not limited to, birds, and the like. The term "individual" does not denote a particular age or sex.

As used herein, "combination therapy" means a first therapy that includes a hepatoprotectant acetaminophen mutual prodrug in conjunction with a second therapy (e.g., surgery and/or an additional pharmaceutical agent) useful for treating, stabilizing, preventing, and/or delaying the disease or condition. Administration in "conjunction with" another compound includes administration in the same or different composition(s), either sequentially, simultaneously, or continuously, through the same or different routes. In one variation, the combination therapy may include a hepatoprotectant acetaminophen mutual prodrug and acetaminophen. In one another variation, the combination therapy may include a hepatoprotectant acetaminophen mutual prodrug and a hepatoprotectant. In some embodiments, the combination therapy optionally includes one or more pharmaceutically acceptable carriers or excipients, non-pharmaceutically active compounds, and/or inert substances.

As used herein, the term "additional pharmaceutical agent," refers to an active agent other than the hepatoprotectant acetaminophen mutual prodrug, for example, a drug, which is administered to elicit a therapeutic effect. The additional pharmaceutical agent(s) may be directed to a therapeutic effect related to the disease or condition that the hepatoprotectant acetaminophen mutual prodrug is intended to treat or prevent (e.g., pain), and/or the pharmaceutical agent may be intended to treat or prevent a symptom of the underlying condition or to reduce the appearance or severity of side effects of administering the hepatoprotectant acetaminophen mutual prodrug.

As used herein, the term "additional pharmaceutical agent," refers to an active agent other than the hepatoprotectant acetaminophen mutual prodrug (e.g., another drug, acetaminophen itself, and/or the hepatoprotectant itself) which is administered to elicit a therapeutic effect. The additional pharmaceutical agent(s) may be directed to (1) a therapeutic effect related to the disease or condition that the hepatoprotectant acetaminophen mutual prodrug is intended to treat or prevent (e.g., pain), (2) treat or prevent a symptom of the underlying condition, (3) reduce the appearance or severity of side effects of administering the hepatoprotectant acetaminophen mutual prodrug, and/or (4) a therapeutic effect related to a disease or condition that is not responsive to hepatoprotectant acetaminophen mutual prodrug or is relatively less responsive to the prodrug (e.g., insomnia, anxiety, depression, inflammation, nausea, and/or vomiting).

Reference to "about" a value or parameter herein includes (and describes) variations that are directed to that value or parameter per se. For example, a description referring to "about X" includes the description of "X".

As used herein and in the appended claims, the singular forms "a," "or," and "the" include plural referents unless the context clearly dictates otherwise. It is understood that aspect and variations of the invention described herein include "consisting" and/or "consisting essentially of" aspects and variations.

Unless defined otherwise or clearly indicated by context, all technical and scientific terms and abbreviations used herein have the same meaning as commonly understood by one of ordinary skill in the art to which this invention belongs.

Hepatoprotectant Acetaminophen Mutual Prodrugs

The invention embraces hepatoprotectant acetaminophen mutual prodrugs which may be useful in the treatment of a disease or condition that is responsive to acetaminophen. The prodrugs contain a hepatoprotectant moiety which may decrease the hepatotoxicity effects resulting from acetaminophen (e.g., acetaminophen induced toxicity in organs, such as the liver, kidneys, and/or heart).

In some embodiments, the hepatoprotectant acetaminophen mutual prodrug comprises an acetaminophen moiety and a hepatoprotectant moiety. The acetaminophen moiety may be covalently linked to the hepatoprotectant moiety at any position suitable for conjugation. The prodrugs may contain a single acetaminophen moiety conjugated to a single hepatoprotectant moiety, a single acetaminophen moiety conjugated to multiple hepatoprotectant moieties, multiple acetaminophen moieties conjugated to a single hepatoprotectant moiety, or multiple acetaminophen moieties conjugated to multiple hepatoprotectant moieties. In some embodiments, the acetaminophen and hepatoprotectant moieties are conjugated at a ratio of 1:1. In some embodiments, the ratio of acetaminophen moiety conjugated to hepatoprotectant moiety is greater than 1:1. In some embodiments, the ratio of hepatoprotectant moiety conjugated to acetaminophen moiety is greater than 1:1.

In some embodiments, the hepatoprotectant acetaminophen mutual prodrug is of formula (I):

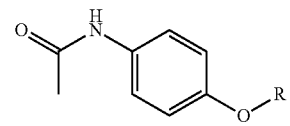

(I)

wherein R is a hepatoprotectant moiety. In some embodiments, the hepatoprotectant acetaminophen mutual prodrug is other than any one, two, or all of 4-acetamidophenyl 2-acetamido4-(methylthio)butanoate; 4-acetamidophenyl 2-acetamido-3-mercaptopropanoate; and 4-acetamidophenyl 2-amino-3-mercaptopropanoate.

In some embodiments, following administration of the hepatoprotectant acetaminophen mutual prodrug to an individual, the acetaminophen moiety is separated from the hepatoprotectant moiety resulting in acetaminophen and a hepatoprotectant compound.

Examples of hepatoprotectant compounds include, but are not limited to, compounds comprising a thiol group or thioether group, such as compounds comprising moieties of the amino acids cysteine or methionine (e.g., a compound with a cysteine and/or methionine radical), or suitable derivatives thereof. Examples of such compounds include cysteine and peptides comprising at least one cysteine, for example, a dipeptide such as GlyCys or tripeptide such as glutathione. In some embodiments, the suitable hepatoprotectant compounds comprise a derivative of cysteine (e.g., 3-acetylcysteine, N-acetyl cysteine, procysteine, or other suitable thiol derived prodrugs cysteine), or a peptide comprising a derivative of cysteine. In some embodiments, the suitable hepatoprotectant compounds comprise a derivative of methionine homocysteine, cystathionine, or other suitable prodrugs of methionine), or a peptide comprising a derivative of methionine. Suitable derivatives of cysteine and methionine include those which either comprise, or are capable of forming in situ, a cysteinyl or methionyl moiety, respectively, or an N-substituted cysteinyl or N-substituted methionyl moiety, respectively.

In some embodiments, each amino acid in the hepatoprotectant acetaminophen mutual prodrug (if present) is in the L-form. In some embodiments, each amino acid (if present) is in the D-form. In some embodiments, the amino acids are in either D- or L-form, but not in racemic form. In some embodiments, the amino acids are in racemic form.

In some embodiments of the present invention, the hepatoprotectant acetaminophen mutual prodrug is of formula (II):

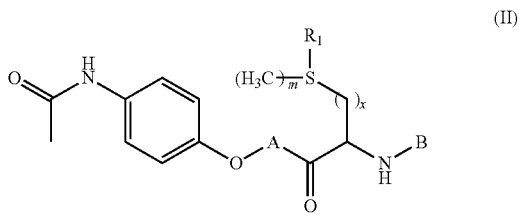

(II)

wherein A is a bond or a substituted or unsubstituted amino acid moiety; B is —H, acetyl, or a substituted or unsubstituted amino acid moiety; $R_1$ is —H, —$CH_3$, an alkylene-phosphate moiety, a substituted or unsubstituted amino acid moiety, or a substituted or unsubstituted nucleoside moiety; or wherein B is taken together with $R_1$ to form a substituted or unsubstituted heterocycloalkyl; x is 1 or 2; and m is 0 or 1 (wherein when m is 1, the sulfur atom is in the form of a sulfonium ion); or a pharmaceutically acceptable salt thereof or solvate of the foregoing. In some of these embodiments, each amino acid moiety is in the D form. In some embodiments, each aminoacid is in the L form.

In some embodiments, the substituted or unsubstituted amino acid moiety is selected from:

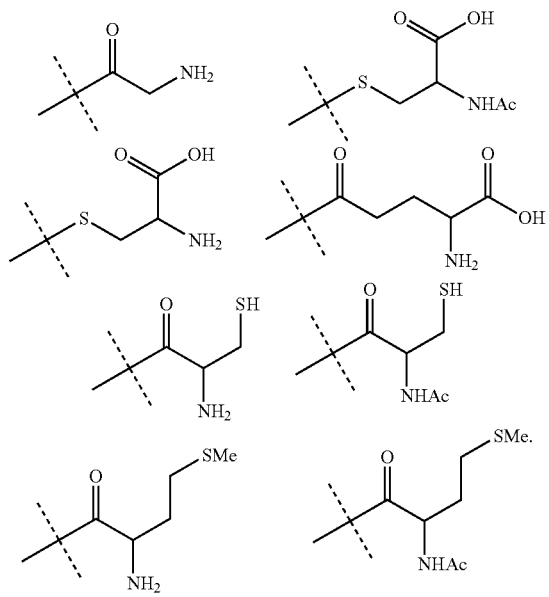

In some of these embodiments, the amino acid moiety is in the D form. In some embodiments, the amino acid is in the L form.

In some embodiments of the compound of formula (II), when A is a bond, x is 1 and $R_1$ is —H, B is —H or a substituted or unsubstituted amino acid moiety. In some embodiments, when A is a bond, x is 1 and $R_1$ is —H, B is a substituted or unsubstituted amino acid moiety. In some embodiments, when A is a bond, x is 2 and $R_1$ is methyl, B is —H or a substituted or unsubstituted amino acid moiety. In some embodiments, when A is a bond, x is 2 and $R_1$ is methyl, B is or a substituted or unsubstituted amino acid moiety. In some embodiments, when A is a bond, and $R_1$ is methyl or B is —H or a substituted or unsubstituted amino acid moiety. In some embodiments, when A is a bond, and $R_1$ is methyl or —H, B is a substituted or unsubstituted amino acid moiety. In some embodiments, the compound is not 4-acetamidophenyl 2-acetamido-4-(methylthio)butanoate, 4-acetamidophenyl 2-acetamido-3-mercaptopropanoate, or 4-acetamidophenyl 2-amino-3-mercaptopropanoate. In some embodiments, the compound is not 4-acetamidophenyl 2-acetamido-4-(methylthio)butanoate. In some embodiments, the compound is not 4-acetamidophenyl 2-acetamido-3-mercaptopropanoate. In some embodiments, the compound is not 4-acetamidophenyl 2-amino-3-mercaptopropanoate.

In some embodiments of the compound of formula (II), A is a bond. In some embodiments, A is a substituted or unsubstituted amino acid moiety. In some embodiments, A is an unsubstituted amino acid moiety. In some embodiments, A is an unsubstituted glycine moiety.

In some embodiments of the compound of formula (II), B is or acetyl. In some embodiments, B is acetyl. In some embodiments, B is —H. In some embodiments, B is a substituted or unsubstituted amino acid moiety. In some embodiments, B is a substituted or unsubstituted glutamate moiety. In some embodiments, B is an unsubstituted glutamate moiety.

In some embodiments of the compound of formula (II), x is 1. In some embodiments, x is 2. In some embodiments, x is 3. In some embodiments, x is 4.

In some embodiments of the compound of formula (II), m is 0. In some embodiments, m is 1.

In some embodiments of the compound of formula (II), $R_1$ is —H, —$CH_3$, or a substituted or unsubstituted amino acid moiety. In some embodiments, $R_1$ is —H, or —$CH_3$. In some embodiments, $R_1$ is —H. In some embodiments, $R_1$ is —$CH_3$. In some embodiments, $R_1$ is a substituted or unsubstituted amino acid moiety (e.g., a substituted or unsubstituted cysteine moiety). In some embodiments, $R_1$ is a substituted or unsubstituted cysteine moiety linked by a disulfide bond. In some embodiments, $R_1$ is an N-acetylcysteine moiety (e.g. an N-acetylcysteine moiety linked by a disulfide bond). In some embodiments, $R_1$ is an alkylenephosphate moiety (e.g., —$CH_2$—$OPO_3H_2$). In some embodiments, $R_1$ is a substituted or unsubstituted nucleoside moiety (e.g., adenosine, guanosine, 5-methyluridine, uridine, or cytidine). In some embodiments, $R_1$ is a substituted or unsubstituted adenosine. In some embodiments, $R_1$ is

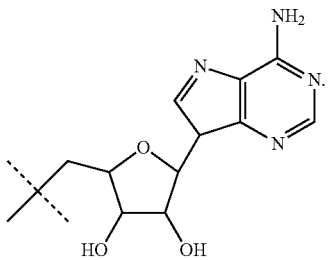

In some embodiments of the compound of formula (II), B is taken together with $R_1$ to form a substituted or unsubstituted heterocycloalkyl. In some embodiments, the heterocycloalkyl is not aromatic. In some embodiments, the heterocycloalkyl comprises sulfur (e.g., thiazolidinonyl). In some embodiments, B is taken together with $R_1$ to form an unsubstituted 5-thiazolidinonyl.

In some embodiments of the compound of formula (II), A and B are each independently a substituted or unsubstituted amino acid moiety. In some of embodiments, $R_1$ is —H, —$CH_3$, or a substituted or unsubstituted amino acid moiety. In some of these embodiments, x is 1 and m is 0.

In some embodiments of the compound of formula (II), only one of A and B is a substituted or unsubstituted amino acid moiety. In some embodiments, $R_1$ is —H, —$CH_3$, or a substituted or unsubstituted amino acid moiety. In some of these embodiments, x is 1 and m is 0.

In some embodiments of the compound of formula (II), A is a bond and B is —H or acetyl. In some embodiments, $R_1$ is —H, —$CH_3$, or a substituted or unsubstituted amino acid moiety. In some of these embodiments, x is 1 and m is 0.

In some embodiments, the compound of formula (II) is of the formula:

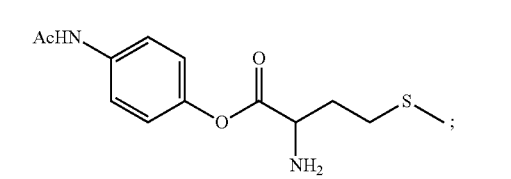

4-acetamidophenyl 2-amino-4-(methylthio)butanoate

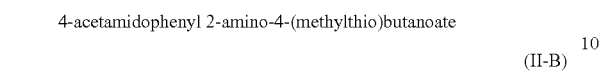

2-acetamido-3-((2-acetamido-3-(4-acetamidophenoxy)-3-oxopropyl)disulfanyl)propanoic acid

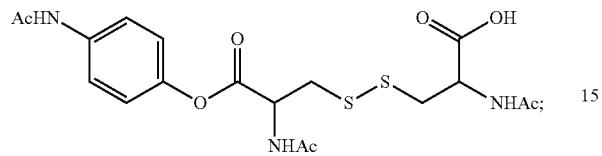

3-((2-acetamido-3-(4-acetamidophenoxy)-3-oxopropyl)disulfanyl)-2-aminopropanoic acid

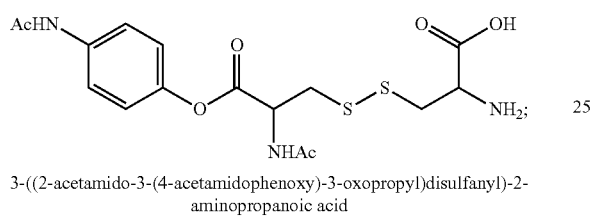

2-acetamido-3-((3-(4-acetamidophenoxy)-2-amino-3-oxopropyl)disulfanyl)propanoic acid

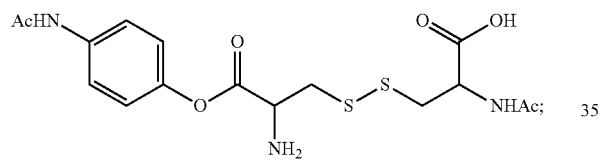

3-((3-(4-acetamidophenoxy)-2-amino-3-oxopropyl)disulfanyl)-2-aminopropanoic acid

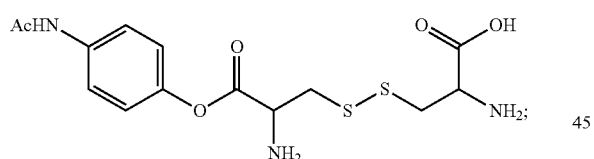

5-(1-(2-(4-acetamidophenoxy)-2-oxoethylamino)-3-mercapto-1-oxopropan-2-ylamino)-2-amino-5-oxopentanoic acid

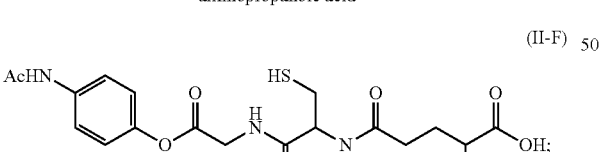

4-acetamidophenyl 2-oxothiazolidine-4-carboxylate

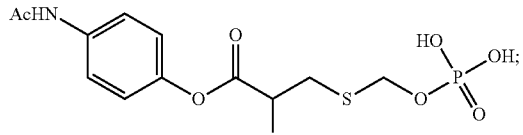

4-acetamidophenyl 2-acetamido-3-(phosphonooxymethylthio)propanoate

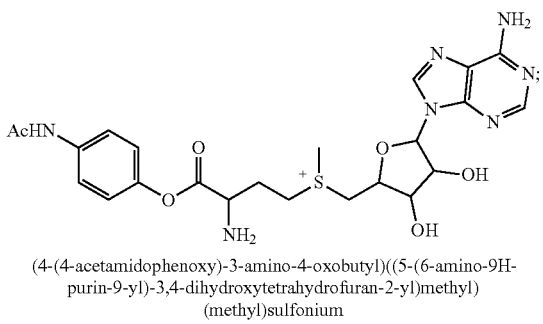

(4-(4-acetamidophenoxy)-3-amino-4-oxobutyl)((5-(6-amino-9H-purin-9-yl)-3,4-dihydroxytetrahydrofuran-2-yl)methyl)(methyl)sulfonium

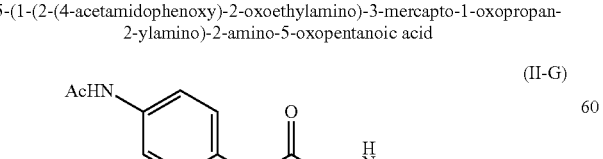

4-acetamidophenyl 2-acetamido-4-(methylthio)butanoate

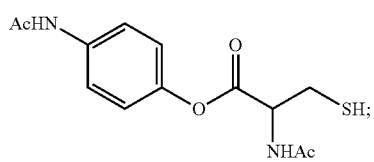

4-acetamidophenyl 2-acetamido-3-mercaptopropanoate

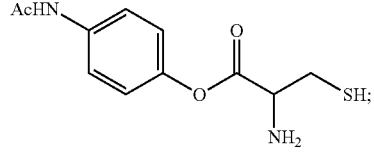

4-acetamidophenyl 2-amino-3-mercaptopropanoate

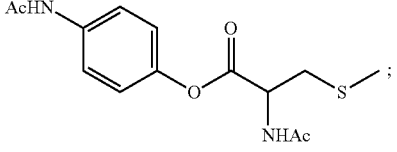

4-acetamidophenyl 2-acetamido-3-(methylthio)propanoate or a pharmaceutically acceptable salt thereof or solvate of the foregoing.

In some embodiments, the hepatoprotectant acetaminophen mutual prodrug is of the formula:

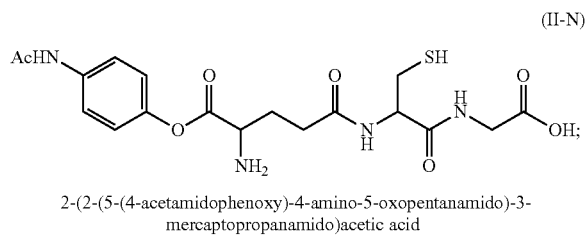 [SMILES: CC(=O)Nc1ccc(OC(=O)C(N)CCC(=O)NC(CS)C(=O)NCC(=O)O)cc1]

2-(2-(5-(4-acetamidophenoxy)-4-amino-5-oxopentanamido)-3-mercaptopropanamido)acetic acid (II-N)

or a pharmaceutically acceptable salt thereof or solvate of the foregoing.

In some embodiments of the present invention, the hepatoprotectant acetaminophen mutual prodrug is of the formula:

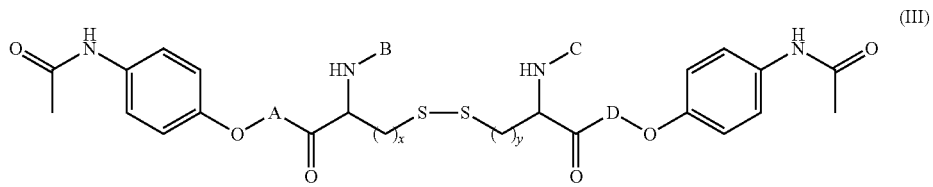

(III)

wherein A and D are each independently a bond or a substituted or unsubstituted amino acid moiety; B and C are each independently —H, acetyl, or a substituted or unsubstituted amino acid moiety; and x and y are each independently 1 or 2; or a pharmaceutically acceptable salt thereof or solvate of the foregoing.

In some embodiments of the compound of formula (III), when A and D are each a bond, x and y are each 1, and B is acetyl, then C is —H, or a substituted or unsubstituted amino acid moiety. In some embodiments, when A and D are each a bond, x and y are each 1, and B is H, then C is acetyl, or a substituted or unsubstituted amino acid moiety. In some embodiments, the compound is not bis(4-acetamidophenyl) 3,3'-disulfanediylbis(2-acetamidopropanoate) or bis(4-acetamidophenyl) 3,3'-disulfanediylbis(2-aminopropanoate). In some embodiments, the compound is not bis(4-acetamidophenyl) 3,3'-disulfanediylbis(2-acetamidopropanoate). In some embodiments, the compound is not bis(4-acetamidophenyl) 3,3'-disulfanediylbis(2-aminopropanoate).

In some embodiments of the compound of formula (III), at least one of A and D is a bond. In some embodiments, each of A and D is a bond. In some embodiments, one of A and D is a bond and the other of A and D is a substituted or unsubstituted amino acid moiety. In some embodiments, at least one of A and D is a substituted or unsubstituted amino acid moiety. In some embodiments, each of A and D is a substituted or unsubstituted amino acid moiety. In some embodiments, A and D are each independently a bond or a substituted or unsubstituted moiety selected from the group consisting of glycine, cysteine, and methionine. In some embodiments, A and D are each independently a substituted or unsubstituted moiety selected from the group consisting of glycine, cysteine, and methionine. In some embodiments, A and D are each independently a substituted or unsubstituted glycine.

In some embodiments of the compound of formula (III), at least one of B and C is H. In some embodiments, each of B and C is H. In some embodiments, at least one of B and C is acetyl. In some embodiments, each of B and C is acetyl.

In some embodiments, one of B and C is H and the other of B and C is acetyl. In some embodiments, B and C are each independently H, acetyl, or a substituted or unsubstituted amino acid moiety selected from the group consisting of glutamate, cysteine, and methionine. In some embodiments, B and C are each independently a substituted or unsubstituted amino acid moiety selected from the group consisting of glutamate, cysteine, and methionine. In some embodiments, B and C are each independently a substituted or unsubstituted glutamate.

In some embodiments of the compound of formula (III), x and y are each 1, In some embodiments, x and y are each 2. In some embodiments, one of x and y is 1 and the other of x and y is 2.

In some embodiments of the compound of formula (III), each amino acid moiety is in the D form. In some embodiments, each amino acid is in the L form. In some embodiments of the compound of formula (III), at least one amino acid moiety is in the D form and at least one amino acid is in the L form.

In some embodiments of the compound of formula (III), A, B, C and D are each independently a substituted or unsubstituted amino acid moiety. In some of these embodiments, A and D are each independently a substituted or unsubstituted moiety selected from the group consisting of glycine, cysteine, and methionine; and B and C are each independently a substituted or unsubstituted amino acid moiety selected from the group consisting of glutamate, cysteine, and methionine. In some of these embodiments, x and y are each 1.

In some embodiments of the compound of formula (III), A and D are each a bond, and B and C are each independently a substituted or un substituted amino acid moiety. In some embodiments, A and D are each independently a substituted or unsubstituted amino acid moiety, and B and C are each independently —H or acetyl. In some embodiments, A is a bond, D is a substituted or unsubstituted amino acid moiety, B is a substituted or unsubstituted amino acid moiety, and C is —H or acetyl. In some of these embodiments, x and y are each 1.

In some embodiments of the compound of formula (III), A and D are each a bond, and B and C are each independently —H or acetyl. In some of these embodiments, x and y are each 1.

In some embodiments, the compound of formula (III) is of the formula:

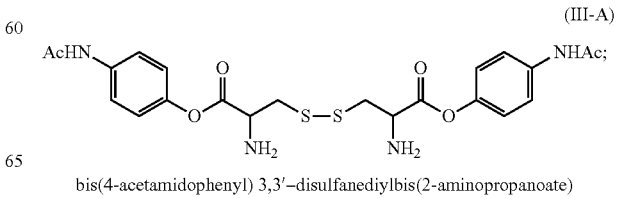

(III-A)

bis(4-acetamidophenyl) 3,3'-disulfanediylbis(2-aminopropanoate)

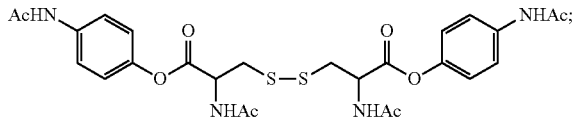

bis(4-acetamidophenyl) 3,3'–disulfanediylbis(2-acetamiopropanoate)

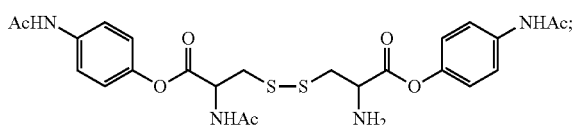

4-acetamidophenyl 2-acetamido-3-((3-(4-acetamidophenoxy)-2-amino-3-oxopropyl)disulfanyl)propanoate (III-D)

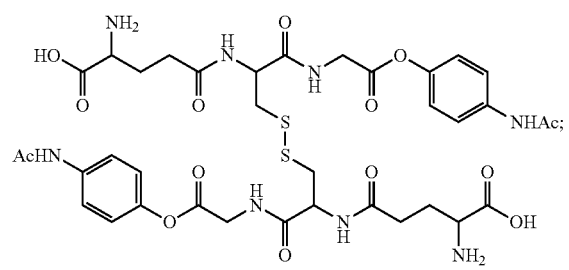

5,5'-(3,3'-disulfanediylbis(1-(2-(4-acetamidophenoxy)-2-oxoethylamino)-1-oxopropane-3,2-diyl))bis(azanediyl)bis(2-amino-5-oxopentanoic acid)

or a pharmaceutically acceptable salt thereof or solvate of the foregoing.

In some embodiments, the hepatoprotectant acetaminophen mutual prodrug is of the formula:

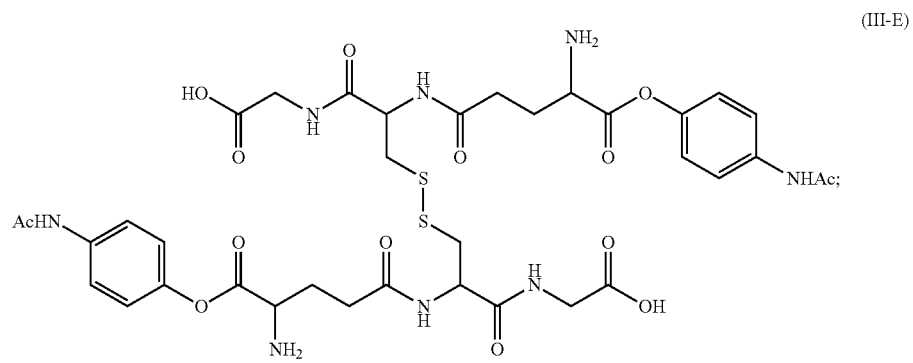 [SMILES: CC(=O)Nc1ccc(OC(=O)C(N)CCC(=O)NC(CSSCC(NC(=O)CCC(N)C(=O)Oc2ccc(NC(C)=O)cc2)C(=O)NCC(=O)O)C(=O)NCC(=O)O)cc1]

or a pharmaceutically acceptable salt thereof or solvate of the foregoing.

In some embodiments, the hepatoprotectant acetaminophen mutual prodrug (e.g., any compound of formula I, II, and/or III) is in substantially pure form. Unless otherwise stated, "substantially pure" intends a preparation of the prodrug that contains no more than 15% impurity, wherein the impurity intends compounds other than the acetaminophen prodrug, but does not include other forms of the prodrug (e.g., different salt or non-salt versions of the prodrug), acetaminophen, and/or the hepatoprotectant. In one variation, a preparation of substantially pure prodrug is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

The invention also embraces all of the solvate, hydrate and/or salt (e.g., pharmaceutically acceptable salt) forms of the hepatoprotectant acetaminophen mutual prodrug described herein and methods of using the same. In some embodiments, the hepatoprotectant acetaminophen mutual prodrug of the present invention can exist in unsolvated forms as well as solvated forms (i.e., solvates). The prodrugs may also include hydrated forms (i.e., hydrates).

The invention embraces all salts of the hepatoprotectant acetaminophen mutual prodrugs described herein (e.g., any compound of formula I, II, and/or III), as well as methods of using such salts of the prodrugs. The invention also embraces all non-salt forms of any salt of a prodrug described herein, as well as other salts of any salt of a prodrug named herein. In some embodiments, the salts of the prodrugs are pharmaceutically acceptable salts. "Pharmaceutically acceptable salts" are those salts which retain the biological activity of the free prodrugs and which can be administered as drugs or pharmaceuticals to an individual (e.g., a human). In some embodiments, the hepatoprotectant acetaminophen mutual prodrugs are mono- or di-substituted by alkali metal or alkaline earth metals. In some embodiments, the hepatoprotectant acetaminophen mutual prodrug is a mono alkaline phosphate salt (e.g., mono sodium phosphate salt). In some embodiments, the hepatoprotectant acetaminophen mutual prodrug is a di-alkaline phosphate salt (e.g., disodium phosphate salt). The desired salt of a basic functional group of a compound may be prepared by methods known to those of skill in the art by treating the compound with an acid. The desired salt of an acidic functional group of a compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, bismuth salts, and calcium salts; ammonium salts; and aluminum salts. Examples of organic salts of acid compounds include, but are not limited to, procaine, dibenzylamine, N-ethylpiperidine, N,N'-dibenzylethylenediamine, trimethylamine, and triethylamine salts. Examples of inorganic salts of base compounds include, but are not limited to, hydrochloride and hydrobromide salts. Examples of organic salts of base compounds include, but are not limited to, tartrate, citrate, maleate, fumarate, and succinate.

In some embodiments, the hepatoprotectant acetaminophen mutual prodrug (e.g., any compound of formula I, II, and/or III) and/or the hepatoprotectant are capable of stimulating synthesis of glutathione (oxidized and/or reduced) under physiological conditions. In some embodiments, the glutathione level (oxidized and/or reduced) in an individual is increased to an amount greater than about 2%, or about 5%, or about 10%, or about 15%, or about 20%, or about 25%, or about 30%, or about 35%, or about 40%, or about 45%, or about 50%, or about 60%, or about 70%, or about 80%, or about 90% compared to blood glutathione levels in the individual without treatment of the hepatoprotectant acetaminophen mutual prodrug or compared to glutathione levels following administration of a molar equivalent acetaminophen under the same conditions. The glutathione level may be the total glutathione level in an individual or glutathione blood level.

In some embodiments, the hepatoprotectant acetaminophen mutual prodrug (e.g., any compound of formula I, II, and/or III) and/or the hepatoprotectant sufficiently decreases hepatotoxicity from the metabolite N-acetyl-p-benzoquinone imine (NAPQI) in an individual relative to the hepatotoxicity from NAPQI following administration of a molar equivalent of acetaminophen administered under the same conditions.

In some embodiments, the hepatoprotectant acetaminophen mutual prodrug (e.g., any compound of formula I, II, and/or III) and/or the hepatoprotectant is capable of inactivating N-acetyl-p-benzoquinone imine (NAPQI). In some embodiments, the hepatoprotectant acetaminophen mutual prodrug and/or the hepatoprotectant sufficiently inactivates N-acetyl-p-benzoquinone imine (NAPQI) in an individual relative to a molar equivalent of acetaminophen administered under the same conditions. In some embodiments, the hepatoprotectant acetaminophen mutual prodrug and/or the hepatoprotectant inactivates NAPQI by at least about 10%, or about 15%, or about 20%, or about 25%, or about 30%, or about 35%, or about 40%, or about 45%, or about 50%, or about 55%, or about 60%, or about 70%, or about 80%, or about 90% relative to a molar equivalent of acetaminophen administered under the same conditions. In some embodiments, the conditions comprise a toxic dose of acetaminophen. In some embodiments, the NAPQI is inactivated by the hepatoprotectant covalently binding to NAPQI (e.g., to generate an acetaminophen-methionine and/or acetaminophen-cysteine conjugates). In some embodiments, the NAPQI is inactivated without the hepatoprotectant covalently binding to NAPQI (e.g., by enhancing glutathione levels and/or levels of acetaminophen-glutathione conjugate).

In some embodiments, the hepatoprotectant acetaminophen mutual prodrugs of the invention (e.g., any compound of formula I, II, and/or III) have increased water solubility relative to acetaminophen. For example, the HCl salt of (S)-4-acetamidophenyl 2-amino-4-(methylthio)butanoate (S-enantiomer and HCl salt of compound (II-A)) has a water solubility at room temperature of more than 30 times that of acetaminophen (=500 mg/mL and about 14.3 mg/ML, respectively). Likewise, compound II-D (2-acetamido-3-((3-(4-acetamidophenoxy)-2-amino-3-oxopropyl)disulfanyl)propanoic acid and its sodium salt were found to have water solubility at room temperature of 47 mg/mL and 52 mg/mL, respectively. Increased water solubility may render the prodrugs more suitable for parenteral administration and may also permit a higher blood level concentration, if desired, and/or allow a lower dosage (and/or a lower dose volume in the case of parenteral formulation) to obtain a similar blood level concentration when compared to acetaminophen. In some embodiments, the prodrugs comprise a charged moiety (e.g., a phosphate and/or an amine). In some embodiments, the prodrugs are greater than 2, 3, 5, 10, 15, 25, 50, 100, 200, 500 or 1000 times more soluble in water than acetaminophen under the same conditions.

In some aspects, the hepatoprotectant acetaminophen mutual prodrugs described herein (e.g., any compound of formula I, II, and/or III) release acetaminophen and the hepatoprotectant following administration to an individual. In certain embodiments, release of acetaminophen and the hepatoprotectant occurs, e.g., in the post-operative setting. In certain aspects, high concentration formulations (e.g., formulation of a high amount of prodrug in a low volume) are provided.

Following administration, in some embodiments (particularly those involving high concentration formulations) rapid release of acetaminophen results in high acetaminophen doses and equivalent hepatoprotectant doses) in a short time period. Exposure to high acetaminophen doses alone may result in undesired hepatotoxicity. Thus, the hepatoprotectant moiety is particularly beneficial in this aspect by providing protection form hepatotoxicity. Post-operative patients or other individuals with compromised systems may particularly benefit from the hepatoprotectant acetaminophen mutual prodrugs described herein.

The hepatoprotectant acetaminophen mutual prodrugs described herein (e.g., any compound of formula I, II, and/or III) may be relatively stable under some conditions (e.g., during storage and/or preparation in a saline solution), while being converted to acetaminophen under other conditions (e.g., following introduction into an in vitro or in vivo system, such as administration into an individual). In some embodiments, the hepatoprotectant acetaminophen mutual prodrug (e.g., a prodrug of formula I, II, and/or III at, for example, about 0.3 ng/mL, or about 15 ng/mL, in plasma, or between about 0.3 ng/mL or about 15 ng/mL in plasma) is capable of greater than 10%, or 15%, or 20%, or 25%, or 30%, or 35%, or 40%, or 45%, or 50%, or 60%, or 75% conversion to acetaminophen after about any of 1 min, 5 min, 10 min, 15 min, 20 min, or 30 min, or 45 min, or 1 hr at 37° C. In some embodiments, the hepatoprotectant acetaminophen mutual prodrug (e.g., a prodrug of formula II-A at, for example, about 0.3 ng/mL or about 15 ng/mL in human plasma, or between about 0.3 ng/mL or about 15 ng/mL in human plasma) is capable of greater than about 30%, or about 45% conversion to acetaminophen after about 10 min at 37° C. In some of these embodiments, the acetaminophen prodrugs are not capable of said conversion to acetaminophen in water, propylene glycol and/or saline at room temperature. For example, in some of these embodiments, the prodrug is not capable of more than any of about 5%, or 10%, or 20%, or 25%, or 30% or 40%, or 60%, or 70% conversion to parent drug at 30 min or 60 min in water or propylene glycol at room temperature. In one embodiment, the acetaminophen prodrug of formula I, II, and/or III at a concentration of about 15 ng/ML (or about 0.3 ng/mL, or between about 0.3 ng/mL, and about 15 ng/mL) in human plasma at 37° C. is capable of greater than 30% conversion to the parent drug at 10 min, and is not capable at the same concentration in water at room temperature of more than 30% conversion at 10 min. In some embodiments, the hepatoprotectant acetaminophen mutual prodrug (e.g., the prodrug of formula and/or is capable of at least 10%, 20%, 30%, 40%, 50%, 60%, 70%, 80%, or 90% increased conversion to acetaminophen in human plasma at 37° C. compared to water at room temperature after the same time of exposure.

Synthetic Methods

The compounds of the invention may be prepared using a number of methods familiar to one of skill in the art. The discussion below is offered to illustrate certain methods available for use in assembling the compounds of the invention and is not intended to limit the scope of the reactions or reaction sequences and/or conditions that are useful in preparing compounds of the invention.

Some target compounds of the invention may be synthesized by starting with readily available acetaminophen as shown below. Scheme I illustrates the preparation of a moiety (such as methionine) by protection of the primary amine with a suitable protecting group (e.g., Boc protection, using Boc$_2$O under basic conditions). The amine can alternatively be acetylated under conditions known in the art to generate acetyl variants of the invention. The carboxylate of the methionine can then be conjugated to acetaminophen using conditions and coupling agents readily known in the art, such as O-(Benzotriazol-1-yl)-N,N,N,N'-tetramethyluronium tetrafluoroborate (TBTU) with a mild base (e.g., N,N'-Diisopropylethylamine (DIPEA)) and subsequently deprotected under acidic conditions, such as HCl or TFA.

Thiols (e.g., from cysteine moieties) can be coupled to create disulfide linkages using an oxidation agent (e.g., N-Chlorosuccinimide (NCS)) as shown below in Scheme II. As shown, the oxidation can occur following coupling of a cysteine residue to acetaminophen, or prior to coupling of the acetaminophen moiety (as shown in Scheme III).

Scheme II.

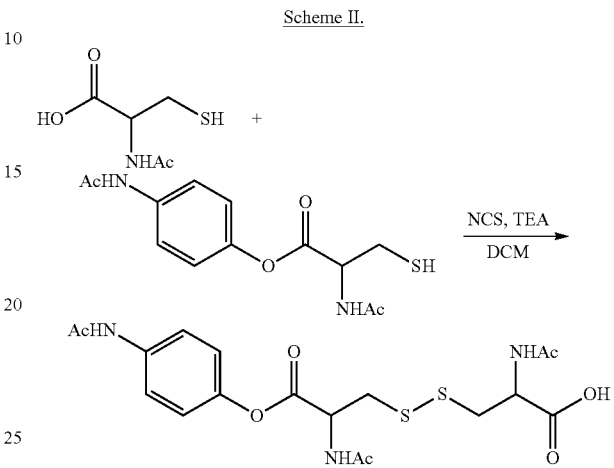

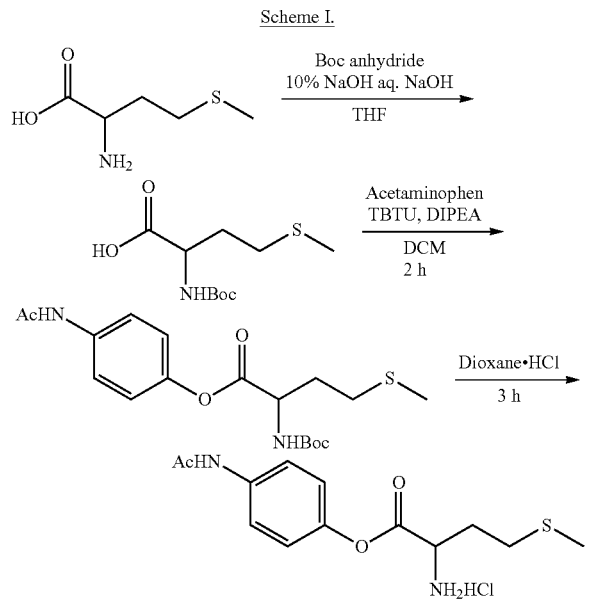

As shown in Scheme III, some target compounds of the invention may be synthesized by first oxidizing cysteine or cysteine derivatives to generate the desired dimer, then conjugating to acetaminophen using conditions and coupling agents known in the art, such as O-(Benzotriazol-1-yl)-N,N,N',N'-tetramethyluronium tetrafluoroborate (TBTU) with a mild base (e.g., N,N,N',N'-Diisopropylethylamine (DIPEA)). The amount of coupling may vary depending on the number of available free carboxylate moieties or stoichimetric ratio of acetaminophen used, as readily determined by one of skill in the art. Product mixtures can be easily separated, then treated under acidic conditions (e.g., HCl or TFA) to provide the desired salt.

Scheme III.

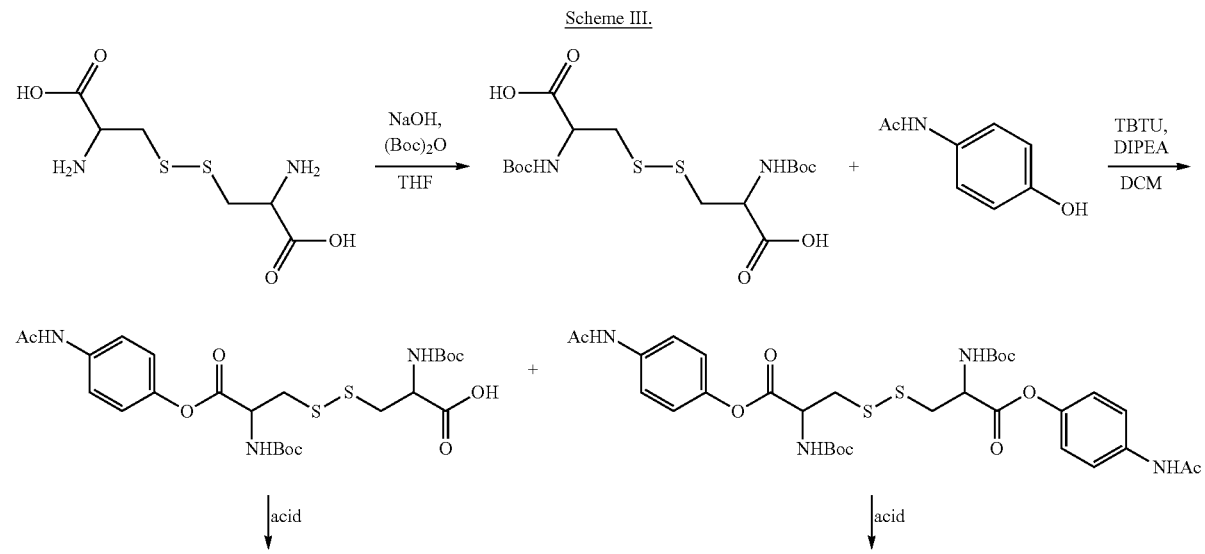

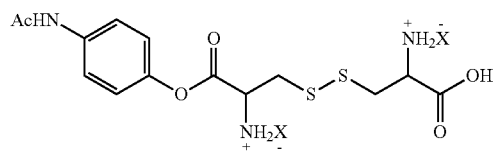
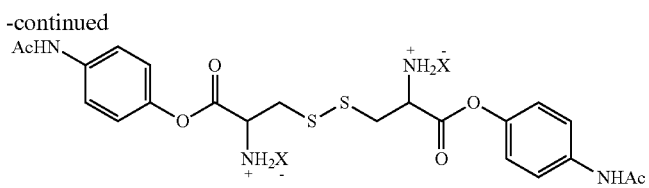

Formulations

The hepatoprotectant acetaminophen mutual prodrug described herein (e.g., any compound of formula I, II, and/or III) can be in formulations (including pharmaceutical compositions) with additives such as excipients (e.g., one or more excipients), antioxidants (e.g., one or more antioxidants), stabilizers (e.g., one or more stabilizers), preservatives (e.g., one or more preservatives), pH adjusting and buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents, viscosity-increasing agents (e.g., one or more viscosity-increasing agents), and the like, either atone or together with one or more additional pharmaceutical agents, provided that the additional components are pharmaceutically acceptable for the particular disease or condition to be treated. In some embodiments, the formulation may include combinations of two or more of the additional components as described herein (e.g., 2, 3, 4, 5, 6, 7, 8, or more additional components). In some embodiments, the additives include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Marck Pub. Co., New Jersey 18$^{th}$ edition (1996), and REMINGTON: THE SCIENCE AND PRACTICE OF PHARMACY, Lippincott Williams & Wilkins, Philadelphia, 20$^{th}$ edition (2003) and 21$^{st}$ edition (2005).

The formulations may vary or be tailored according to the condition to be treated, the amount of compound to be administered, the condition of the individual, and other variables that will readily be apparent to one of ordinary skill in the art in view of the teachings provided herein.

In some embodiments, the formulation (e.g., formulations amenable to parenteral administration) is an aqueous formulation with a pH from about 3.5 to about 9.5, or from about 4.5 to about 8.5, or from about 5.0 to about 9.0, or from about 5.5 to about 8.5, or from about 6.0 to about 8.0, or from about 6.5 to about 8.0, or from about 7.0 to about 8.0, or about 7.4.

Formulations comprising a hepatoprotectant acetaminophen mutual prodrug described herein (e.g., any compound of formula I, II, and/or III) and saline are provided. In one aspect, such formulations are at physiological pH (about 7.4). Such formulations may be amenable to storage and subsequent use with the prodrug remaining intact for prolonged periods of time (e.g., during storage) and converted to acetaminophen after administration to an individual (e.g., an adult, child, or infant). In some embodiments, the prodrug is stored as a dry powder and the formulation is generated by dissolving the dry powder in saline prior to administration. In one aspect, prodrug formulations are provided, e.g., formulations comprising the molar equivalent of about any of 50 mg/mL, 75 mg/mL, 100 mg/mL, 125 mg/mL, 150 mg/mL, 175 mg/mL, or 200 mg/mL of acetaminophen, wherein molar equivalent is the amount of prodrug that would result in the indicated amount of acetaminophen upon complete conversion. For any amount e.g., dosage) of hepatoprotectant acetaminophen mutual prodrug described herein, also contemplated is the molar prodrug equivalent for that amount of acetaminophen. Single bolus formulations are also provided, e.g., up to about any of 5 mL, 10 mL, or 15 mL (at, for example, the molar prodrug equivalent of about 1450 mg to about 1600 mg of acetaminophen).

Kits

The invention also provides kits containing materials useful for the treatment or prevention of a condition that is responsive to acetaminophen (e.g., pain). The kits may contain a hepatoprotectant acetaminophen mutual prodrug described herein any compound of formula I, II, and/or III) and instructions for use. The kits may comprise a container with a label. Suitable containers include, for example, bottles, vials, and test tubes. The containers may be formed from a variety of materials such as glass or plastic. The containers may hold a prodrug or a formulation of a prodrug (e.g., a formulation further comprising one or more additional pharmaceutical agents). The label on the container may indicate that the hepatoprotectant acetaminophen mutual prodrug or the formulation is used for treating or suppressing a condition that is responsive to acetaminophen (e.g., pain), and may also indicate directions for either in vivo or in vitro use, such as those described herein. The label may further indicate that the prodrug may be administered in doses greater than those permitted for acetaminophen (e.g., prodrug molar equivalent of greater than 4 g per day acetaminophen). The label may further note that the prodrug is also a hepatoprotectant to acetaminophen induced hepatotoxicity.

The invention also provides kits comprising one or more of the hepatoprotectant acetaminophen mutual prodrugs described herein (e.g., any compound of formula I, II, and/or III) of the invention. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, to treat an individual with one or more conditions responsive to acetaminophen (e.g., pain and/or fever), or to suppress one or more such conditions.

In certain embodiments the kits may include a dosage amount of at least one formulation as disclosed herein. In one aspect, dosage forms correspond to dose that exceed the molar equivalent of 4 g/day of acetaminophen. Kits may also comprise a means for the delivery of the formulation thereof.

The kits may include additional pharmaceutical agents for use in conjunction with the formulation described herein. In some variations, the additional pharmaceutical agent(s) may be one or more analgesic drug(s). These agents may be provided in a separate form, or mixed with the compounds of the present invention, provided such mixing does not reduce the effectiveness of either the pharmaceutical agent or formulation described herein and is compatible with the route of administration. Similarly the kits may include additional agents for adjunctive therapy or other agents known to the skilled artisan as effective in the treatment or prevention of the conditions described herein.

The kits may optionally include appropriate instructions for preparation and/or administration of a formulation comprising a hepatoprotectant acetaminophen mutual prodrug of the invention. Information detailing possible side effects of the formulation, and any other relevant information may also be enclosed. The instructions may be in any suitable format, including, but not limited to, printed matter, videotape, computer readable disk, optical disc or directions to internet-based instructions.

In another aspect of the invention, kits for treating an individual who suffers from or is susceptible to the disease or conditions described herein are provided, comprising a first container comprising a dosage amount of a composition as disclosed herein, and instructions for use. The container may be any of those known in the art and appropriate for storage and delivery of intravenous formulation. In certain embodiments the kit further comprises a second container comprising a pharmaceutically acceptable carrier, diluent, adjuvant, etc. for preparation of the formulation to be administered to the individual.

Kits may also be provided that contain sufficient dosages of the compounds described herein (including formulations thereof) to provide effective treatment for an individual for an extended period, such as 1-3 days, 1-5 days, a week, 2 weeks, 3, weeks, 4 weeks, 6 weeks, 8 weeks, 3 months, 4 months, 5 months, 6 months, 7 months, 8 months, 9 months or more.

The kits may include the composition as described herein packaged in either a unit dosage form or in a multi-use form. The kits may also include multiple units of the unit dose form.

Methods of Treatment

The hepatoprotectant acetaminophen mutual prodrug of the present invention (e.g., any compound of formula I, II, and/or III) may be used to treat a disease or condition that is responsive to acetaminophen (e.g., pain and/or fever). In one embodiment, the invention provides a method of treating a disease or condition that is responsive to acetaminophen comprising administering to an individual an effective amount of a hepatoprotectant acetaminophen mutual prodrug. In some embodiments, the individual is at risk of developing a disease or condition that is responsive to acetaminophen. In some embodiments are provided methods of treating pain, fever, inflammation, ischemic injury (such as myocardial and/or cerebral), or neuronal injury in an individual, comprising administering to the individual an effective amount of a hepatoprotectant acetaminophen mutual prodrug. In one variation, the individual is post-operative and has or is believed to have or developed post-operative pain. In one variation, the prodrug is administered prophylactically for post-operative pain. In one variation, the individual is not amenable to oral administration of acetaminophen.

The invention embraces methods of treating pain of any etiology, including acute and chronic pain, and any pain in which acetaminophen analgesic is prescribed. Examples of pain include post-surgical pain, post-operative pain (including dental pain), migraine, headache and trigeminal neuralgia, pain associated with burn, wound or kidney stone, pain associated with trauma (including traumatic head injury), neuropathic pain (e.g., peripheral neuropathy and postherpetic neuralgia), pain associated with musculo-skeletal disorders, strains, sprains, contusions, fractures, such as myalgia, rheumatoid arthritis, osteoarthritis, cystitis, pancreatitis, inflammatory bowel disease, ankylosing spondylitis, sero-negative (non-rheumatoid) arthropathies, non-articular rheumatism and peri-articular disorders, and pain associated with cancer (including "break-through pain" and pain associated with terminal cancer). Examples of pain with an inflammatory component (in addition to some of those described above) include rheumatic pain, pain associated with mucositis, and dysmenorrhea. In some variations, the methods and formulations of the present invention are used for treatment or prevention of post-surgical pain and cancer pain. In some variations, the methods and compositions of the present invention are used for treatment or prevention of pain that is selected from the group consisting of pain associated with surgery, trauma, osteoarthritis, rheumatoid arthritis, lower back pain, fibromyalgia, postherpetic neuralgia, diabetic neuropathy, HIV-associated neuropathy and complex regional pain syndrome.

In some variations, the methods and compositions of the present invention (e.g., any compound of formula I, II, and/or III) are used for treatment or prevention of pain and/or fever (e.g., in adults, children and/or infants). In some embodiments, the methods and compositions of the present invention (e.g., any compound of formula I, II, and/or III) are used for treatment of pain, such as acute pain (e.g., acute pain following surgery, such as orthopedic surgery of adults, children, and/or infants). In some embodiments, the methods and compositions of the present invention (e.g., any compound of formula I, II, and/or III) are used for treatment or prevention of fever, such as endotoxin-induced fever (e.g., endotoxin-induced fever in adults, children, and/or infants). In some embodiments, the methods and compositions of the present invention (e.g., any compound of formula I, II, and/or III) are used for treatment or prevention of fever in children and/or infants. In some embodiments, the fever is selected from low-grade fever, moderate fever, high-grade fever and hyperpyrexia fever. In some embodiments, the fever is selected from Pel-Ebstein fever, continuous fever, intermittent fever, and remittent fever.

In some variations of the methods, the hepatotoxicity, potential hepatotoxicity, and/or amount of hepatotoxins in an individual following administration of the hepatoprotectant acetaminophen mutual prodrug (e.g., any compound of formula I, and/or III) is reduced relative to administration of acetaminophen under the same conditions. In some variations, the toxic effects or potential toxic effects on the liver of the individual following administration of the hepatoprotectant acetaminophen mutual prodrug (e.g., any compound of formula I, II, and/or III) is reduced relative to administration of acetaminophen under the same conditions.

In some variations of the methods, the hepatotoxicity from the metabolite N-acetyl-p-benzoquinone imine (NAPQI) in an individual following administration of the hepatoprotectant acetaminophen mutual prodrug (e.g., any compound of formula I, II, and/or III) is reduced relative to administration of acetaminophen under the same conditions.

In some variations of the methods, the hepatoprotectant acetaminophen mutual prodrug (e.g., any compound of formula I, II, and/or III) inactivates N-acetyl-p-benzoquinone imine (NAPQI). In some embodiments, the amount of inactivated NAPQI in an individual following administration of the hepatoprotectant acetaminophen mutual prodrug (e.g., any compound of formula I, II, and/or III) is increased (and the level of NAPQI is decreased) relative to administration of acetaminophen under the same conditions. In some embodiments, the amount of inactivated NAPQI is increased by at least about 10%, or about 15%, or about 20%, or about 25%, or about 30%, or about 35%, or about 40%, or about 45%, or about 50%, or about 55%, or about 60%, or about 70%, or about 80%, or about 90% relative to administration of acetaminophen under the same conditions. In some embodiments, the conditions comprise a toxic dose of acetaminophen. In some embodiments, the NAPQI is inactivated by the hepatoprotectant covalently binding to NAPQI (e.g., to generate an acetaminophen-methionine and/or acetaminophen-cysteine conjugates). In some embodiments, the NAPQI is inactivated without the hepatoprotectant covalently binding to NAPQI (e.g., by enhancing glutathione levels and/or levels of acetaminophen-glutathione conjugate).

In some variations of the methods, the hepatoprotectant moiety of the compound stimulates synthesis of glutathione (oxidized and/or reduced) under physiological conditions. In some embodiments, the blood glutathione level (oxidized and/or reduced) in an individual is increased to an amount greater than about 2%, or about 5%, or about 10%, or about 15%, or about 20%, or about 25%, or about 30%, or about 35%, or about 40%, or about 45%, or about 50% or about 60%, or about 70%, or about 80%, or about 90% compare to blood glutathione levels in the individual without treatment of the hepatoprotectant acetaminophen mutual prodrug.

The invention embraces methods of reducing the level of hepatotoxicity of acetaminophen in an individual, comprising administering to the individual a hepatoprotectant acetaminophen mutual prodrug (e.g., any compound of formula I, II, and/or III). The invention also embraces methods of reducing the level of liver toxicity of acetaminophen in an individual, comprising administering to the individual a hepatoprotectant acetaminophen mutual prodrug (e.g., any compound of formula I, II, and/or III). In some of these methods, hepatotoxicity is reduced while concurrently treating the individual for a disease or condition that is responsive to acetaminophen (e.g., pain and/or fever).

In some embodiments, the invention embraces methods of delaying the onset of acetaminophen and/or hepatoprotectant action in an individual in need of acetaminophen and/or hepatoprotectant therapy, the method comprising administering to the individual an effective amount of a hepatoprotectant acetaminophen mutual prodrug (e.g., any compound of formula I, II, and/or III) wherein the prodrug provides a slower onset of acetaminophen and/or hepatoprotectant action as compared to acetaminophen and/or the hepatoprotectant. In one variation, administration of the a hepatoprotectant acetaminophen mutual prodrug (e.g., any compound of formula I, II, and/or III) delays the onset of action of acetaminophen and/or the hepatoprotectant by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours as compared to administration of acetaminophen. In some embodiments, the invention embraces little or no delay in the onset of acetaminophen and/or hepatoprotectant action compared to acetaminophen and/or the hepatoprotectant.

In some embodiments, the invention embraces methods of prolonging acetaminophen and/or hepatoprotectant activity in an individual in need of acetaminophen and/or hepatoprotectant therapy, the method comprising administering to the individual an effective amount of a hepatoprotectant acetaminophen mutual prodrug (e.g., any compound of formula I, II, and/or III) wherein the prodrug provides prolonged acetaminophen and/or hepatoprotectant activity as compared to acetaminophen and/or the hepatoprotectant. In one variation, administration of the hepatoprotectant acetaminophen mutual prodrug (e.g., any compound of formula I, II, and/or III) prolongs activity of acetaminophen and/or the hepatoprotectant by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours as compared to administration of the acetaminophen and/or the hepatoprotectant. In some embodiments, the invention embraces little or no prolonging of acetaminophen and/or hepatoprotectant activity compared to administration of acetaminophen and/or the hepatoprotectant.

In some embodiments, the invention embraces a method of providing acetaminophen and a hepatoprotectant to an individual, the method comprising administering hepatoprotectant acetaminophen mutual prodrug (e.g., any compound of formula I, II, and/or III), wherein the prodrug converts to acetaminophen and a hepatoprotectant. Also provided are methods of providing acetaminophen and a hepatoprotectant to an individual by administering a hepatoprotectant acetaminophen mutual prodrug (e.g., any compound of formula I, II, and/or III), where the prodrug converts to acetaminophen and a hepatoprotectant in vivo. In one aspect, the prodrug (e.g., any compound of formula I, II, and/or III) results in conversion to acetaminophen within about 1, 5, 10, 15, or 30 min following administration. Conversion may be measured by techniques known in the art, including those detailed in the Experimental section herein. In some embodiments, the invention embraces methods of providing acetaminophen and a hepatoprotectant to an individual (e.g., an individual in need of acetaminophen and/or hepatoprotectant therapy), the method comprising administering to the individual an effective amount of a hepatoprotectant acetaminophen mutual prodrug (e.g., any compound of formula I, II, and/or III) wherein greater than about any of 10%, or 15%, or 20%, or 25%, or 30%, or 35%, or 40%, or 45%, or 50%, or 60%, or 75% or 85%, or 90%, or 95% of the prodrug is converted to acetaminophen and the hepatoprotectant after less than about any of 1 min, 3 min, 5 min, 10 min, 20 min, or 30 min, or 45 min, or 1 hr following administration. In some embodiments, the method comprises administering to the individual an effective amount of a hepatoprotectant acetaminophen mutual prodrug (e.g., any compound of formula I, II, and/or III) wherein greater than about 10% or about 20% of the prodrug is converted to acetaminophen and the hepatoprotectant after less than about 1 min or about 3 min following administration.

In some embodiments, the invention embraces a method of providing acetaminophen and a hepatoprotectant to an individual (e.g., an individual in need of acetaminophen and/or hepatoprotectant therapy), the method comprising administering to the individual (e.g., intravenously) an effective amount of a hepatoprotectant acetaminophen mutual prodrug (e.g., any compound of formula I, II, and/or III) wherein the resulting concentration of acetaminophen (e.g., at about any of 10 min, or 20 min, or 30 min, or 45 min, or 1 hr, or 2 hr, or 3 hr following administration) is within less than about any of 50%, or 40%, or 30%, or 25%, or 20%, or 15%, or 10%, or 5% when compared to the administering acetaminophen alone under the same conditions. For example, in some embodiments, methods of providing acetaminophen and a hepatoprotectant to an individual in need of acetaminophen and/or hepatoprotectant therapy are provided, the methods comprising intravenously administering to the individual an effective amount of a hepatoprotectant acetaminophen mutual prodrug (e.g., any compound of formula I, II, and/or III) wherein the resulting concentration of acetaminophen or metabolite thereof (e.g., at about 30 min or 1 hr following administration) is within less than about 15% or about 5% when compared to administering acetaminophen alone under the same conditions.

Methods of providing higher doses of acetaminophen than may be safely provided by administration of acetaminophen alone are also provided. In one aspect, acetaminophen is provided by administering a hepatoprotectant acetaminophen mutual prodrug (e.g., any compound of formula I, II, and/or III) in a dose and over a time period unsafe for acetaminophen (and/or formulations of acetaminophen) under the same conditions. For example, methods of providing greater than 4 g/day of acetaminophen are provided by administering a hepatoprotectant acetaminophen mutual prodrug (e.g., any compound of formula I, II, and/or III). In one aspect, methods employ liquid formulations (e.g., saline). Methods may also employ difference formulations (e.g., IV administration followed by oral doses).

Combination Therapy

The hepatoprotectant acetaminophen mutual prodrugs of the present invention (e.g., any compound of formula I, II, and/or III) may be formulated and/or administered in conjunction with one or more additional pharmaceutical agents, as described herein and as known in the art, including one or more additional pharmaceutical agents to further reduce the occurrence and/or severity of symptoms and/or clinical manifestations thereof, as well as additional pharmaceutical agents that treat or prevent the underlying conditions, or in conjunction with (e.g., prior to, concurrently with, or after) additional treatment modalities. The hepatoprotectant acetaminophen mutual prodrugs as described herein may be administered before, concurrently with, or after the administration of one or more of the additional pharmaceutical agents. The prodrugs described herein may also be administered in conjunction with (e.g., prior to, concurrently with, or after) agents to alleviate the symptoms associated with either the condition or the treatment regimen.

In some embodiments of the formulations and methods of the present invention, the prodrugs are used in combination with one or more additional pharmaceutical agents. Representative additional pharmaceutical agents include opioids (natural, semi-synthetic, or synthetic), non-steroidal anti-inflammatory drugs (NSAIDs), benzodiazepines, barbiturates and other compounds, such as caffeine. Examples of compounds contemplated for combination with prodrug of current invention include, but are not limited to, codeine, morphine, hydrocodone, hydromorphone, levorphanol, aspirin, ketorolac, ibuprofen, ketoprofen, flurbiprofen, etodolac, diclofenac, misoprostol, meloxicam, piroxicam, naproxen, caffeine, doxylamine, pamabrom, tramadol, dextropropoxyphene, methylhexital, carisoprodol, butalbital, diazepam, lorazepam, and midazolam. One potential advantage of combination formulation is that the formulation may induce analgesia beyond the ceiling effect of acetaminophen without necessity to approach the toxic or nearly toxic dose levels of acetaminophen. Combinations of the acetaminophen prodrugs with benzodiazepines such as diazepam, lorazepam, midazolam or any other benzodiazepines, may be used for treatment of pre- and postoperative anxiety in addition to the treatment of e.g., analgesia. Such combination may be particularly useful in dental surgeries (e.g., mole extraction).

The above additional pharmaceutical agents to be employed in combination with the hepatoprotectant acetaminophen mutual prodrugs of the invention may be used in therapeutic amounts, such as those indicated in the PHYSICIANS' DESK REFERENCE (PDR) 53rd Edition (1999), or such therapeutically useful amounts as would be known to one of ordinary skill in the art.

Additional pharmaceutical agents (e.g., analgesic drugs) administered with one or more of the hepatoprotectant acetaminophen mutual prodrugs of the present invention (e.g., any compound of formula I, II, and/or III) can be administered at the recommended maximum clinical dosage or at lower doses. Dosage levels of the additional pharmaceutical agents in the formulations of the invention may be varied so as to obtain a desired therapeutic response depending on the route of administration, severity of the disease and the characteristics and response of the patient. The combination can be administered as separate formulations or as a single dosage form containing both agents. When administered as a combination, the prodrugs can be formulated as separate formulations, which are given at the same time or different times, or the prodrugs, can be given as a single formulation.

As will be well appreciated by the skilled artisan, for particular conditions, different additional pharmaceutical agent(s) and/or additional treatment modality(ies) may be employed.

In some embodiments, a hepatoprotectant acetaminophen mutual prodrug of the current invention may be formulated and/or administered with acetaminophen and/or a hepatoprotectant itself. Such combination therapy may provide an initial therapeutic amount of acetaminophen and/or the hepatoprotectant, followed by a delayed and/or prolonged parent drug activity and/or hepatoprotectant activity from the prodrug. Such formulations may permit a decreased dosing frequency. Alternatively, an initial dose of hepatoprotectant acetaminophen mutual prodrug (e.g., as a low volume, high concentration dose to treat post-operative pain and/or fever) may be followed by administration of acetaminophen to treat pain and/or fever, and/or followed by administration of a hepatoprotectant (e.g., after discharge from a hospital or surgical setting).

The formulations and methods described herein may be used alone or in conjunction with (e.g., prior to, concurrently with, or after) other modes of treatments (e.g., adjunctive therapy with additional pharmaceutical agents described herein with reference to pharmaceutical formulations of the claimed compounds or known to the skilled artisan) used to treat or prevent the condition being treated/prevented and/or administration of an additional treatment modality, or combinations of the foregone). For example, in combination with one or more additional pharmaceutical agents as described herein and known to those of skill in the art and/or currently available treatment modalities, including, for example, surgery or radiotherapy. As used herein, the term "additional treatment modality" refers to treatment/prevention of the conditions described herein without the use of a pharmaceutical agent (e.g., surgery, radiotherapy, etc.). Where combinations of pharmaceutical agent(s) and/or additional treatment modality(ies) are used, they may be, independently, administered prior to, concurrently with, or after administration of one or more of the hepatoprotectant acetaminophen mutual prodrugs (or formulation(s) thereof) as described herein.

The optimal combination of one or more additional treatment modalities and/or additional pharmaceutical agents in conjunction with administration of the formulations described herein, can be determined by an attending physician or veterinarian based on the individual and taking into consideration the various factors effecting the particular individual, including those described herein.

Dosing and Methods of Administration

The hepatoprotectant acetaminophen mutual prodrugs of the present invention (e.g., any compound of formula I, II, and/or III) and formulations described herein will generally be used in an amount effective to achieve the intended result, for example in an effective amount to treat or prevent the particular condition being treated or prevented (e.g., pain and/or fever). The amount of the prodrug or formulation administered in order to administer an effective amount will depend upon a variety of factors, including, for example, the particular condition being treated, the frequency of administration, the particular formulation being administered, the severity of the condition being treated and the age, weight and general health of the individual, the adverse effects experienced by the individual being treated, etc. Determination of an effective dosage is within the capabilities of those skilled in the art, particularly in view of the teachings provided herein. Dosages may also be estimated using in vivo animal models. In one aspect, the dosage is greater than that recommended for the molar equivalent of acetaminophen (e.g., prodrug dosage greater than the molar equivalent of 4 g/day acetaminophen). For example, in one aspect, the dosage is greater than the molar equivalent of 4, 5, 6, 7, 8, or 10 g/day acetaminophen.

The amount of hepatoprotectant acetaminophen mutual prodrugs of the present invention that may be combined with the carrier materials to produce a single dosage form may vary depending upon the host to which the prodrug is administered and the particular mode of administration, in addition to one or more of the variety of factors described above. A pharmaceutical unit dosage chosen may be fabricated and administered to provide a defined final concentration of drug in the blood, tissues, organs, or other targeted region of the body. The effective amount for a given situation can be readily determined by routine experimentation and is within the skill and judgment of the ordinary clinician.

In some embodiments, the toxic dosage (e.g., $LD_{50}$ or NOAEL (No Observed Adverse Effect Level)) of the hepatoprotectant acetaminophen mutual prodrug. (e.g., any compound of formula I, II, and/or III) may be higher than the molar equivalent toxic dosage of acetaminophen. In some embodiments, the toxic dosage of the prodrug is 1.2, 2, 5, 7.5, 10, 15, 20, 50, 100, 250, 500, or 1000 times higher than the molar toxic dosage of acetaminophen.

In some embodiments, the dosage of the hepatoprotectant acetaminophen mutual prodrug (e.g., any compound of formula I, II, and/or III) required to obtain the same blood level concentration as acetaminophen is lower due to the increased solubility of the prodrug. In some embodiments, the required dosage of the prodrug to obtain the same blood level concentration as the acetaminophen is 1.2, 2, 5, 7.5, 10, 15, 20, 50, or 100 times lower than acetaminophen.

Examples of hepatoprotectant acetaminophen mutual prodrug dosages (e.g., any compound of formula I, II, and/or III, alone or in combination with an additional pharmaceutical agent) which can be used are an effective amount within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds of the present invention may be administered, alone or in combination, in a single daily dose, or the total daily dosage may be administered in divided dosage of two, three, four, five, or six times daily.

The frequency and duration of administration of the hepatoprotectant acetaminophen mutual prodrug will depend on the condition being treated, the condition of the individual, and the like. The formulation may be administered to the individual one or more times, for example, 2, 3, 4, 5, 10, 15, 20, or more times. The formulation may be administered to the individual, for example, more than, equal to, or less than once a day, 2 times a day, 3 times a day, or more than 3 times a day; or 1-6 times a day, 2-6 times a day, or 4-6 times a day. The formulation may also be administered to the individual, for example, less than once a day, for example, every other day, every third day, every week, or less frequently. The formulation may be administered over a period of days, weeks, or months.

The hepatoprotectant acetaminophen mutual prodrugs of the invention may be administered enterally (e.g., orally or rectally), parenterally (e.g., by injection (such as intravenously or intramuscularly), or by inhalation (e.g., as mists or sprays)), or topically, in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g., via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The prodrugs may be mixed with pharmaceutically acceptable carriers, adjuvants, and vehicles appropriate for the desired route of administration. The route of administration may vary according to the condition to be treated. Additional methods of administration are known in the art.

In some embodiments of the methods, the route of administration for hepatoprotectant acetaminophen mutual prodrugs of the invention (e.g., any compound of formula I, II, and/or III) is oral. In some embodiments, formulations are suitable for oral administration. The prodrugs described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such formulations may also comprise adjuvants, such as wetting agents, emulsifying and suspending agents, cyclodextrins, and sweetening, flavoring, and perfuming agents.

In some embodiments, the hepatoprotectant acetaminophen mutual prodrugs of the invention (e.g., any compound of formula I, II, and/or III) are administered parenterally (e.g., intravenously or intramuscularly). Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. The sterile injectable preparation may also be a sterile powder to be reconstituted using acceptable vehicles prior to administration. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables.

In some embodiments are provided high doses of hepatoprotectant acetaminophen mutual prodrug in a low volume (e.g., in a low volume of saline). Non-limiting examples of an effective amount (e.g., for parenteral administration, such as intravenous or intramuscular), include the prodrug at a dosage range of from about 20 mg per day to about 22 g per day, or from about 60 mg per day to about 15 g, or from about 200 mg per day to about 11 g, or from about 300 mg to about 3.6 g per day, or from about 500 mg to about 3.6 g per day, of from about 750 mg to about 3.6 g. In some embodiments, the effective amount for parenteral (e.g., intravenous or intramuscular) administration is a dose range about of about 0.01 µmol to about 100 mmol, or about 0.1 µmol to about 75 mmol, or about 0.5 µmol to about 50 mmol, or about 1 µmol to about 50 mmol, or about 1 µmol to about 10 mmol, or about 5 µmol to about 50 mmol, or about 10 µmol to about 25 mmol, or about 100 µmol to about 10 mmol, or about 500 µmol to about 5 mmol, or about 0.01 mg to about 20 g, or about 0.1 mg to about 20 g, or about 0.5 mg to about 15 g, or about 1 mg to about 15 g, or about 2 mg to about 10 g, or about 5 mg to about 10 g, or about 10 mg to about 10 g, or about 50 mg to about 7.5 g, or about 100 mg to about 7.5 g, or about 200 mg to about 5 g, or about 500 mg to about 4 g, or about 750 mg to about 3 g, or about 1 g to about 2.5 g, or about 1.3 g to about 1.9 g, and may be administered in about 1 mL, to about 1000 mL, or about 1 mL to about 500 mL, or about 1 mL to about 100 mL, or about 1 mL to about 50 mL about 1 to about 30 mL, or about 1 mL to about 25 mL, or about 5 mL to about 20 mL, or about 5 mL to about 15 mL or about 10 mL to about 15 mL, or about 5 mL to about 10 mL. In some embodiments, the effective amount for parenteral (e.g., intravenous or intramuscular) administration is a dose range of about 0.1 µmol/kg to about 1000 µmol/kg, or about 5 µmol/kg to about 750 µmol/kg, or about 7.5 µmol/kg to about 500 µmol/kg, or about 10 µmol/kg to about 100 µmol/kg, or about 25 µmol/kg to about 75 µmol/kg. In some of these embodiments, the prodrug (e.g., any compound of formula I, II, and/or III) is administered in a solution at a concentration of about 10 mg/mL to about 1000 mg/mL, or about 25 mg/mL to about 750 mg/mL, or about 50 mg/mL to about 500 mg/mL, or about 75 mg/mL to about 400 mg/mL, or about 100 mg/mL to about 300 mg/mL, or about 150 mg/mL to about 250 mg/mL.

The invention also includes formulations of hepatoprotectant acetaminophen mutual prodrugs administered in the form of suppositories for rectal administration. These can be prepared by mixing the agent with a suitable not irritating excipient that is solid at room temperature but liquid at rectal temperature and therefore will melt in the rectum to release the drug. Such materials include cocoa butter, beeswax and polyethylene glycols.

The hepatoprotectant acetaminophen mutual prodrugs of the invention (e.g., any compound of formula I, II, and/or III) may also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and/or metabolizable lipid capable of forming liposomes may be used. The present formulations in liposome form can contain, in addition to a prodrug, stabilizers, preservatives, excipients, and the like. In some embodiments, the lipids are the phospholipids and/or phosphatidyl cholines (lecithins), natural and/or synthetic. Methods to form liposomes are known in the art. See, for example, Prescott, Ed., *Methods in Cell Biology*, Volume XIV, Academic Press, New York, N.W., p. 33 et seq (1976).

Treatment regimens may include administering hepatoprotectant acetaminophen mutual prodrugs described herein in more than one form, e.g., as art IV administration in a clinical setting followed by oral administration in a non-clinical setting.

EXAMPLES

The present invention will be understood more readily by reference to the following examples, which are provided by way of illustration and are not intended to be limiting of the present invention.

Example 1: Synthesis of (S)-4-acetamidophenyl 2-amino-4-(methylthio)butanoate

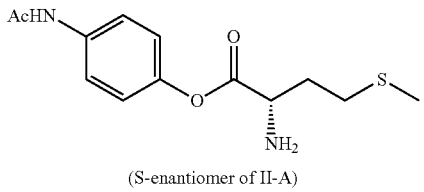 [SMILES: CSCC[C@H](N)C(=O)Oc1ccc(NC(C)=O)cc1]

(S-enantiomer of II-A)

A white color milky suspension of L-methionine (3 g, 20 mmol) in THF (30 mL) and 10% NaOH solution (10 mL) was stirred for 30 min before turning into a clear colorless solution. To this Boc anhydride (6.58 g, 30.1 mmol) was added slowly over about 15 min at RT. The clear colorless solution was stirred further 12 h at RT. The reaction was monitored by TLC (DCM:MeOH (95:5 mL); TLC silica gel 60 $F_{254}$ (Merck), detection with Ninhydrin solution (5% in Methanol); $R_f$ values, product: 0.7, L-methionine: 0). After 12 h the clear colorless solution was turned to light brown color solution. This light brown color solution was evaporated under vacuum; a light brown color gummy material (thick oil) was obtained which was taken into ethyl acetate and water (60 mL: 10 mL); pH of the solution was adjusted to 6 by using 20% citric acid solution (15 mL). The light brown layer of ethyl acetate was separated and dried over sodium sulphate, and fully evaporated to yield a light brown colored gummy material which was washed with ether (2×25 mL), hexane (3×15 mL) and pentane (1×25 mL) to generate a white crystalline solid of Boc-protected Methionine ((S)-2-(tert-butoxycarbonylamino)-4-(methylthio)butanoic acid; 3.5 g; 70% yield).

To a stirring (for 15 minutes) colorless solution of (S)-2-(tert-butoxycarbonylamino)-4-(methylthio)butanoic acid (3.5 g, 14.0 mmol) in DCM (60 mL), was added acetaminophen (N-(4-hydroxyphenyl)acetamide; 2.33 g, 15.4 mmol) and TBTU (9.0 g, 28.11 mol). The colorless solution turned into light yellow color after 20 min, at which point the solution was slowly treated with DIPEA (3.63 g, 28.11 mol). The reaction mixture was stirred for further 2 h at RT and monitored by TLC (MeOH:DCM (1:9); TLC silica gel 60 $F_{254}$ (Merck), detection with λ254 nm UV and ninhydrin solution (5% in methanol); $R_f$ values, Boc-protected L-Methionine: 0.7, acetaminophen: 0.5, product: 0.6). Water (80 mL) was added into the reaction mass and a light yellow layer of dichloromethane was separated and washed with 20% citric acid solution (2×20 mL). The dichloromethane layer was washed with 10% $NaHCO_3$ solution (1×30 mL) and dried over sodium sulphate. A light yellow gummy material was obtained following evaporation. The gummy material was purified by column chromatogram (silica gel) using 5% methanol in dichloromethane as an eluent to generate a white crystalline solid as (S)-4-acetamidophenyl 2-(tert-butoxycarbonylamino)-4-(methylthio)butanoate (3 g; 56% yield).

To a stirred colorless solution of (S)-4-acetamidophenyl 2-(tert-butoxycarbonylamino)-4-(methylthio)butanoate (0.5 g, 1.3 mmol) in dioxane (10 mL) was added 40 mL of HCl in dioxane (4M). The reaction mixture turned into a milky solution, which was stirred for 3 h at RT. The reaction mass was filtered through Whatman filter paper and a white crystalline solid and washed with ether (2×15 mL) to generate deprotected product ((S)-4-acetamidophenyl 2-amino-4-(methylthio)butanoate: 300 mg; 81% yield). $^1H$ NMR (400 MHz, DMSO-d6): δ 10.08 (s, 1H), 8.63 (bs, 1H), 7.64 (d, 2H, J=8.8 Hz), 7.14 (d, 2H, J=8.8 Hz), 4.4 (m, 1H), 2.69 (m, 2H), 2.22 (m, 2H), 2.1 (s, 3H), 2.04 (2, 3H); $^{13}C$ NMR (100 MHz, DMSO-d6): δ168.34, 168.15, 144.76, 137.60, 121.488, 119.89, 51.01, 29.30, 28.41, 23.87, 14.28; MS m/z (APCI): 283 (M+H)$^+$; Melting Point: 225-228° C.; Solubility in water at room temperature: 500 mg/mL

Example 2: Synthesis of 2-acetamido-3-((2-acetamido-3-(4-acetamidophenoxy)-3-oxopropyl)disulfanyl)propanoic acid

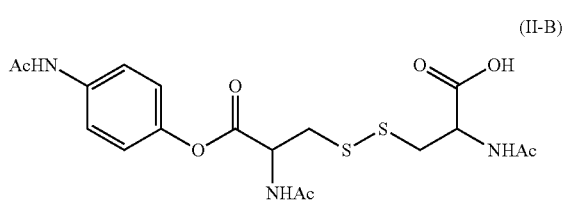 [SMILES: CC(=O)Nc1ccc(OC(=O)C(CSSCC(NC(C)=O)C(=O)O)NC(C)=O)cc1]

To a stirring milky suspension of N-Acetyl cysteine (0.2 g; 1.23 mmol) in DCM (5 mL) at 0° C. was added a catalytic amount of acetic acid followed by N-chlorosuccinimide (0.18 g; 1.35 mmol). The milky suspension was stirred at 0° C. for 30 min. In another round bottom flask, a milky suspension of 4-acetamidophenyl 2-acetamido-3-mercaptopropanoate (0.25 g; 1.23 mmol) in DCM (5.0 mL) and TEA (0.28 mL 2.45 mmol) was prepared and cooled to at 0° C. This milky suspension was added to the above N-Acetyl cysteine suspension. The resulting reaction mixture turned from milky suspension to a clear light orange solution within 15 min of 2.5 hours of stirring at 0° C. The reaction mixture was then evaporated under vacuum at 40° C. to yield light orange syrup, which was washed with diethyl ether (2×20 mL) and finally purified by preparative HPLC to generate a white crystalline solid of 2-acetamido-3-((2-acetamido-3-(4-acetamidophenoxy)-3-oxopropyl)disulfanyl)propanoic acid (20 mg; 10% yield). $^1H$ NMR (400 MHz, DMSO-d6): δ 12.89 (bs, 1H), 9.99 (s, 1H), 8.60 (d, 1H, J=7.2 Hz), 8.29 (d, J=8 Hz), 7.59 (d, 2H, J=9.2 Hz), 7.05 (dd, 2H, J=1.2 Hz, 1.2 Hz), 4.69 (m, 1H), 4.48 (m, 1H), 3.09 (m, 4H), 2.50 (s, 3H), 2.500 (s, 3H), 2.49 (s, 3H). MS m/z (APCI): 458 (M+H)$^+$; Melting Range: 95-99° C.; $R_f$ value, product: O,N-Acetyl cysteine: 0, 4-acetamidophenyl 2-acetamido-3-mercaptopropanoate: 0.5 (Methanol:Dichloromethane; (10:90); TLC silica gel 60 $F_{254}$ (Merck); Detection with λ254 nm UV).

Example 3: Synthesis of 3-((3-(4-acetamidophenoxy)-2-amino-3-oxopropyl)disulfanyl)-2-aminopropanoic acid dihydrochloride

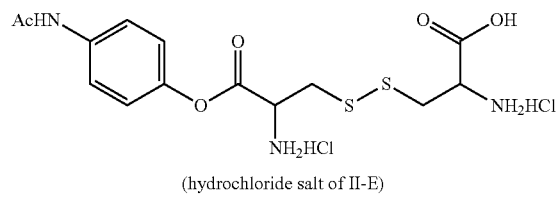

(hydrochloride salt of II-E)

To a stirring colorless suspension of disulfide-linked cysteine (3,3'-disulfanediylbis(2-aminopropanoic acid), 5 g; 20.80 mmol) in THF (50 mL) was added 10% NaOH solution (25 mL) and stirred for 15 mints at RT. After 15 minutes, colorless suspension turned to a clear colorless solution, which was cooled to 0° C. and Boc anhydride (13.6 g; 62.42 mmol) was added. The reaction mass was warmed to RT and stirring continued for 12 hours. The reaction was monitored by TLC (methanol:dichloromethane (20:80); TLC silica gel 60 $F_{254}$ (Merck); detection with λ254 nm UV; $R_f$ values, starting material: 0, boc-protected starting material; 0.2). After the reaction was completed, the reaction mixture was evaporated to dryness. The crude compound was taken into DI water (20 mL) and washed with ethyl acetate (50 mL). The ethyl acetate layer was removed and the aqueous layer was acidified to pH 6 by 20% citric acid solution (30 mL) and extracted with ethyl acetate (2×75 mL). Combined ethyl acetate extracts were dried over sodium sulphate and concentrated under vacuum to yield a light orange viscous mass, which was purified by washing with hexane (3×50 mL), and diethyl ether (100 mL) to generate 3,3'-disulfanediylbis(2-(tert-butoxycarbonylamino)propanoic acid) as a white solid, (9 g; 98.3% yield).

A colorless suspension of 3,3'-disulfanediylbis(2-(tert-butoxycarbonylamino)propanoic acid) (5 g; 11.36 mmol) in dry DCM (120 mL) was treated with acetaminophen (3.4 g; 22.72 mmol) and TBTU (7.29 g; 22.72 mmol) followed by addition of DIPEA (2.9 g; 22.72 mmol) after one hour. The colorless suspension turned into a light yellow clear solution, which was stirred for further 3 hours at RT. The reaction was monitored by TLC (methanol:dichloromethane (10:90); TLC silica gel 60 $F_{254}$ (Merck); detection with λ254 nm UV; $R_f$ values: 3,3'-disulfanediylbis(2-(tert-butoxycarbonylamino)propanoic acid): 0.2, acetaminophen: 0.4; di-coupled product: 0.5, single-coupled product: 0). After completion of the reaction, DI water was added to reaction mixture and the organic layer was separated, washed with 20% citric acid solution (70 mL), and dried over sodium sulphate. Evaporating the solvent afforded a brown color viscous mass, which was purified by column chromatography (silica gel) using 10% methanol in dichloromethane as an eluent to provide the mixture of bis(4-acetamidophenyl) 3,3'-disulfanediylbis(2-(tert-butoxycarbonylamino)propanoate) and 3-((3-(4-acetamidophenoxy)-2-(tert-butoxycarbonylamino)-3-oxopropyl)disulfanyl)-2-(tert-butoxycarbonylamino)propanoic acid. The mixture was further purified by prep HPLC to afford 0.5 g (7% yield) of the desired 3-((3-(4-acetamidophenoxy)-2-(tert-butoxycarbonylamino)-3-oxopropyl)disulfanyl)-2-(tert-butoxycarbonylamino)propanoic acid as an off-white solid.

To a stirring off-white suspension of 3-((3-(4-acetamidophenoxy)-2-(tert-butoxycarbonylamino)-3-oxopropyl)disulfanyl)-2-(tert-butoxycarbonylamino)propanoic acid (20 mg; 0.03 mmol) in diethyl ether (10 mL), was added ether-HCl solution (3 mL). The reaction mass was stirred at RT for 6 hr and reaction progress was monitored by TLC (methanol: dichloromethane (10:90) TLC silica gel 60 $F_{254}$ (Merck); detection with λ254 nm UV; $R_f$ values: starting material: 0 and product: 9). Following reaction completion by TLC, the reaction mixture was evaporated and an off-white solid was obtained. This solid was washed with diethyl ether (2×15 mL), methanol (5 mL) and diethyl ether ((5 mL) to afford 3-((3-(4-acetamidophenoxy)-2-amino-3-oxopropyl)disulfanyl)-2-aminopropanoic acid dihydrochloride (5 mg, 33% yield) as an off-white solid. $^1$H NMR (400 MHz, DMSO-$d_6$): δ 10.13 (s, 1H), 8.75 (bs, 4H), 7.6 (d, 2H, 8.8 Hz), 7.15 (d, 2H, J=8.8 Hz), 4.63 (t, 3H), 4.22 (t, 1H), 3.40-3.16 (m, 4H), 2.05 (s, 3H). MS m/z (APCI): 373 (M+H)$^+$; Melting Range: 230 to 237° C.

Example 4: Synthesis of bis(4-acetamidophenyl)3,3'-disulfanediylbis(2-aminopropanoate)di(trifluoroacetate)

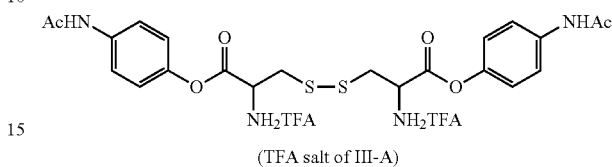

(TFA salt of III-A)

To a stirring, off-white suspension of bis(4-acetamidophenyl) 3,3'-disulfanediylbis(2-(tert-butoxycarbonylamino)propanoate) (0.1 g; 0.14 mmol: obtained from the preparation described in Example 3) in DCM (10 mL) was added 0.2 mL TFA (0.32 g, 2.84 mmol). The reaction mixture was stirred at RT for 12 hours and reaction progress was monitored by TLC (methanol:dichloromethane ((0:90) TLC silica gel 60 $F_{254}$ (Merck); detection with λ254 nm UV; $R_f$ values, starting material: 0.5, product: 0). Following completion by TLC, the reaction mass was evaporated to obtain an off-white solid which was washed with diethyl ether (2×15 mL), methanol (5 mL), and diethyl ether (15 mL) affording 50 mg bis(4-acetamidophenyl) 3,3'-disulfanediylbis(2-aminopropanoate) di(trifluoroacetate) (50% yield) as an off-white solid. $^1$H NMR (400 MHz, DMSO-$d_6$): δ 10.05 (s, 1171), 7.63 (d, 2H, J=8.4 Hz), 7.11 ((d, 2H, J=8.4 Hz), 4.5 (m, 2H), 3.41 (m, 4H), 2.04 (s, 61-1); MS m/z (APCI): 506.59 (M+H)$^+$; Melting Point: >300° C.

Example 5: Synthesis of (S)-4-acetamidophenyl 2-oxothiazolidine-4-carboxylate

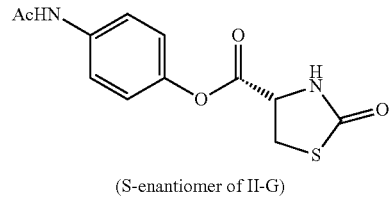

(S-enantiomer of II-G)

To a stirring colorless solution of L-Cysteine (10 g; 82.5 mmol) in 10% NaOH (15 g in 150 mL of deionized water) at 0° C., was slowly added a colorless solution of triphosgene (24 g; 80.9 mmol) dioxane (170 mL) over about 1 hr. Addition resulted in the reaction mixture turning a milky suspension, which was stirred at RT for an additional 3 hr. After 2 hr, this suspension turned to a clear light brown solution. The light brown colored reaction mass was concentrated by rotary evaporator to provide an orange color viscous liquid, which was treated with hot acetonitrile (3×40 mL). The acetonitrile layer was separated and concentrated under vacuum at 48° C. to afford a white solid, which was washed with an acetone:ether mixture (1:4; 3×100 mL). The combined organic layers were separated and concentrated to obtain (S)-2-oxothiazolidine-4-carboxylic acid as a pale yellow solid in 83% yield (10 g).

To a stirring pale yellow suspension of (S)-2-oxothiazolidine-4-carboxylic acid (2 g; 13.6 mmol) in dry dichloromethane (50 mL) at 0° C., was added acetaminophen (2 g; 13.2 mmol) and TBTU (7 g; 21.8 mmol) followed by DIPEA (2.5 mL). The suspension turned into a clear, light-brown solution after 15 min and was stirred at RT for about 3 hr. The reaction was monitored by TLC (dichloromethane:methanol (90:10); TLC silica gel 60 $F_{254}$ (Merck); detection with λ254 nm UV; $R_f$ values, acetaminophen: 0.4, product: 0.5). The reaction was quenched with water (25 mL), and light-brown organic layer was separated from the aqueous layer. This aqueous layer was extracted with ethyl acetate (2×50 mL) and the combined organic layers were washed with water and 10% citric acid (25 mL), dried over sodium sulphate and concentrated to afford a viscous brown liquid. The resulting liquid was washed with diethyl ether (3×25 mL) and acetonitrile (2×10 mL) to afford 250 mg (6.6% yield) of (S)-4-acetanaidophenyl 2-oxothiazolidine-4-carboxylate as a pale yellow solid. $^1$H NMR (400 MHz, DMSO-$d_6$): δ 10.02 (s, 1H), 8.75 (s, 1H), 7.6 (d, 2H, J=8.2 Hz), 7.03 (d, 2H, J=8.2 Hz), 4.8 (m, 1H), 3.84 (m, 1H), 3.75 (m, 1H), 2.02 (s, 3H). $^{13}$C NMR (100 MHz, DMSO-$d_6$): δ 173.13, 170.02, 168.26, 167.43, 153.06, 145.21, 137.31, 121.54, 120.75, 119.88, 114.93, 55.48, 31.47, 23.87, 23.68. MS m/z (APCI): 281 (M+H)$^+$.

Figure 2:
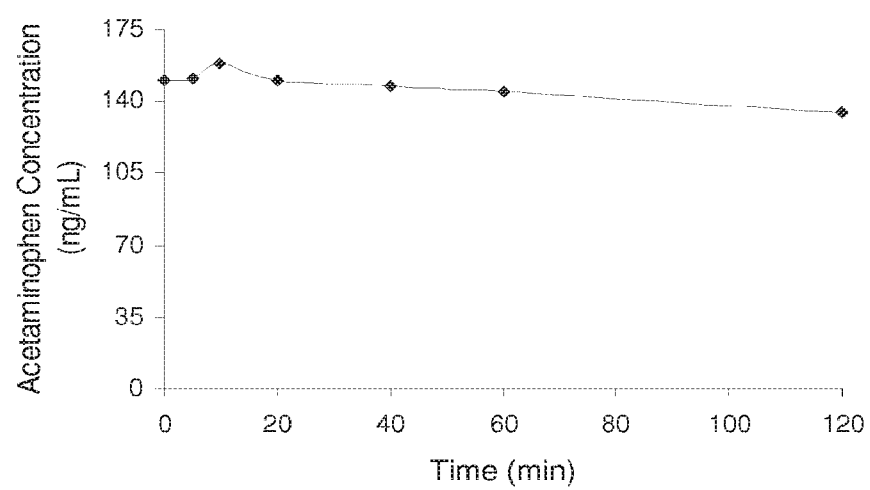
FIG. 2 shows the formation of acetaminophen from 0.3 µg/mL if compound (II-A) in human plasma.

Example 6: In Vitro Conversion of Acetaminophen Prodrug Compound (II-A) to Acetaminophen A known amount of Compound (II-A) was incubated with human plasma samples maintained at physiological temperature. Small aliquots were drawn at predefined time points (0, 5, 10, 15, 20, 25, 30, 40, 60 and 120 minutes) and analyzed for acetaminophen content. The experiment was performed with two different concentrations of prodrug (15 µg/mL and 0.3 µg/mL) in pooled human plasma at 37° C. to determine kinetics of metabolic reaction and whether or not saturation of enzymatic system involved in conversion of prodrug to acetaminophen drug takes place. It was found that acetaminophen appeared rapidly by the time of first sample collection at nominal 0 minutes, as shown in FIGS. 1 and 2.

Example 7: In Vivo Conversion of Acetaminophen Prodrug Compound (II-A) to Acetaminophen Conversion of acetaminophen prodrug to acetaminophen through metabolism in the body was studied in rats. Similar to experimental design described above for in vitro studies, the compound of formula (II-A) was intravenously administered to the test animal and blood is drawn at predefined time points. The blood was analyzed for acetaminophen content, and the half-life of prodrug was determined.

Figure 3:
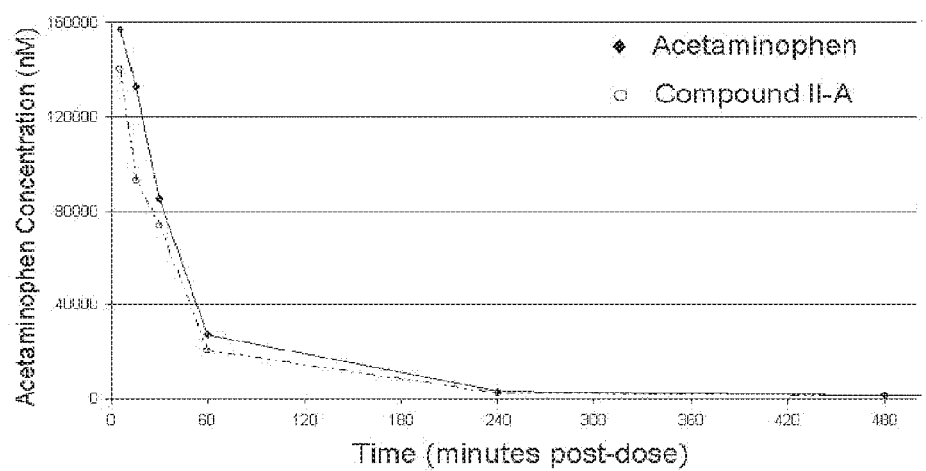
FIG. 3 shows the time-dependent plasma concentration of acetaminophen from compound (II-A) compared to the parent drug acetaminophen.

The pharmacokinetics of acetaminophen and the HCl salt of the compound of formula (II-A) were evaluated after intravenous (IV) administration to determine resulting plasma acetaminophen concentrations Acetaminophen and the HCl salt of the compound (II-A) were dosed on an equimolar basis to provide the same level of exposure (25 mg/kg) to acetaminophen and to obtain the profile of compound (II-A) conversion in vivo to acetaminophen. The test animals were male and female Sprague Dawley (CD® IGS) rats (Charles River Laboratories), 7 to 8 weeks of age, weighing 220 to 270 grams. The rats were serially bled at 7 at time points: 5, 15, 30 minutes and 1, 4, 8 and 24 hours post-dose. Whole blood samples (300 µl) were collected from the tail vein in lithium heparin microcontainers, processed to plasma by centrifugation and plasma was stored frozen at −70° C. until analyzed. Results of plasma analyses for acetaminophen content are shown in FIG. 3 and Table 1.

TABLE 1

Summary of calculated pharmacokinetic parameters of acetaminophen after intravenous administration of Compound (II-A) to rats

| PK Parameter | Acetaminophen | | Compound (II-A) | |
|---|---|---|---|---|
| | Mean | % CV | Mean | % CV |
| Dose (mg/kg) | 25 | N.A. | 25* | N.A. |
| Half life (hr) | 2.65 | 43.7 | 1.87 | 53.2 |
| $T_{max}$ (hr) | 0.139 | 62.2 | 0.083 | 0.00** |
| $C_{max}$ (ng/mL) | 26467 | 22.8 | 26367 | 23.2 |
| $AUC_{0-8}$ (hr · ng/mL) | 24300 | 33.6 | 19250 | 25.8 |
| Clearance (mL/min/kg) | 19.5 | 40.5 | 23.0 | 27.8 |
| $V_{ss}$ (L/kg) | 1.48 | 25.0 | 1.65 | 31.8 |

*molar equivalent of 25 mg/kg acetaminophen
**all values the same

Example 8: Hepatoprotection of Acetaminophen Prodrugs

Studies were undertaken to evaluate the potential hepatoprotection provided by the l-methionine released by Compound (II-A) when administered orally to mice. An appropriate mouse strain was selected and the time course of acute acetaminophen-induced hepatotoxicity was determined. Hepatotoxicity was evaluated by measuring standard plasma enzymatic markers (Alanine transaminase (ALT) and Aspartate transaminase (AST)) of liver damage.

The first step was to identify a mouse strain which shows consistent signs of acute hepatoxicity following oral administration of acetaminophen. Both Swiss Albino and C57BL6 mice were studied and the C57BL6 strain was selected. Next, the time course of acute acetaminophen-induced hepatotoxicity was determined by dosing acetaminophen at 250 mg/kg and collecting plasma samples at 8, 12 and 24 hours. A clear increase in ALT and AST levels were observed in all mice at the 12-hour time point. Consequently, this time point was used in all subsequent studies. Next, a minimally effective acetaminophen dose level was determined. C57BL6 male mice were fasted overnight and dosed orally with acetaminophen at dose levels of 170 and 365 mg/kg and blood was collected 12 hours after dosing. As both dose levels produced distinct elevations of ALT and AST levels, 170 mg/kg acetaminophen was selected for subsequent studies.

In order to provide evidence that equimolar doses of l-methionine (167 mg/kg) prevent acetaminophen-induced hepatotoxicity, co-administration of equimolar doses l-methionine and acetaminophen were administered. It was observed that oral l-methionine did not affect serum AST and ALT levels, however, co-administration of equimolar doses of l-methionine significantly reduced AST and ALT increases in acetaminophen-treated animals.

Figure 4:
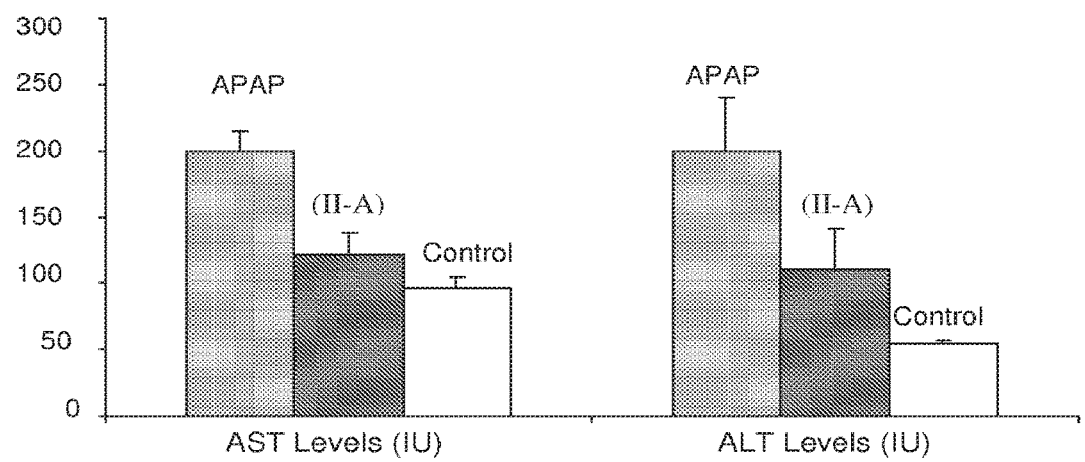
FIG. 4 shows the relative reduction in acute hepatotoxicity with Compound (II-A) when dosed orally to mice.

Finally, the hepatotoxic effects of equimolar dose levels of acetaminophen and Compound (II-A) were compared. In this study, 170 mg/kg acetaminophen was found to be hepatotoxic, as AST levels increased in all treated mice and ALT levels were elevated in 83%. In contrast, oral administration of equimolar dose levels of Compound (II-A) (357.07 mg/kg) displayed average AST and ALT levels significantly less than acetaminophen-treated AST and ALT levels. These data are shown graphically in FIG. 4.

Figure 5:
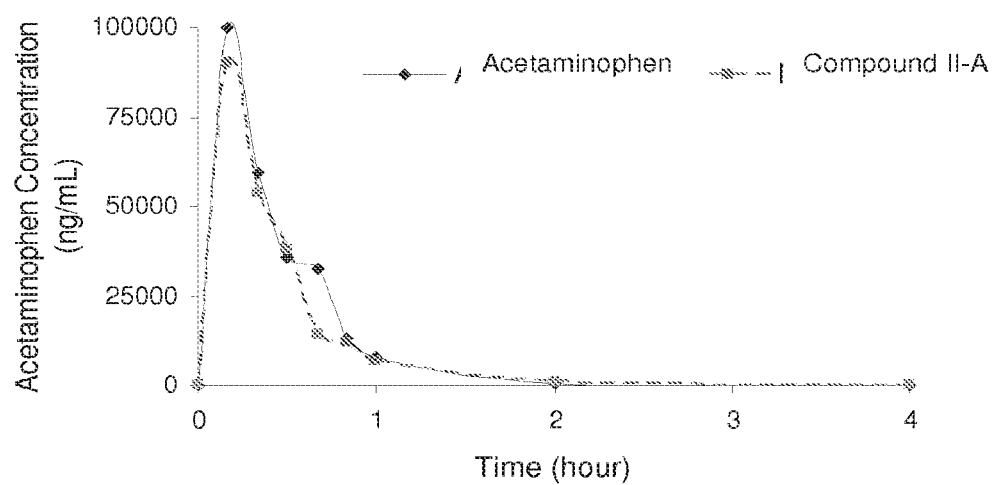
FIG. 5 shows the pharmacokinetic profile of acetaminophen following oral administration of Compound (II-A) and acetaminophen to mice.

In order to confirm that systemic exposure to acetaminophen following Compound (II-A) administration was comparable to that provided by acetaminophen alone, male C57BL6 mice (8 to 12 weeks old) received oral equimolar doses of Compound (II-A) (357 mg/kg) or acetaminophen (170 mg/kg). These data are plotted graphically in FIG. 5 and the calculated pharmacokinetic parameters are presented in Table 2.

TABLE 2

Pharmacokinetic parameters of acetaminophen following oral administration of Compound (II-A) and acetaminophen to mice

| PK Parameter | Acetaminophen | Compound (II-A) |
|---|---|---|
| Dose | 170 mg/kg | 365.67 mg/kg* |
| $T_{max}$ (hr) | 0.167 | 0.167 |
| $C_{max}$ (ng/mL) | 99746.84 | 90050.51 |
| $k_{el}$ (1/hr) | 1.66 | 1.27 |
| $t_{1/2}$ (hr) | 0.42 | 0.55 |
| $AUC_{(0-8)}$ (hr · ng/mL) | 46016.73 | 40528.35 |
| MRT (hr) | 0.48 | 0.49 |

*molar equivalent dose

What is claimed is:

1. A compound of formula (II-A):

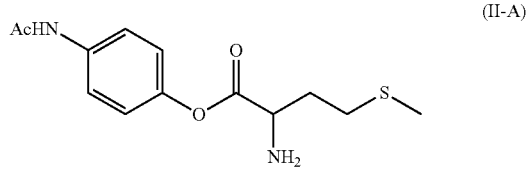 [SMILES: CSCCC(N)C(=O)Oc1ccc(NC(C)=O)cc1]

(II-A)

or a pharmaceutically acceptable salt thereof.

2. A formulation comprising an effective amount of the compound of claim 1, or a pharmaceutically acceptable salt thereof, and a pharmaceutically acceptable carrier.

3. The formulation of claim 2, further comprising a compound selected from the group consisting of an opioid, non-steroidal anti-inflammatory drug (NSAID), benzodiazepine, and barbiturate.

4. The formulation of claim 2, further comprising a compound selected from the group consisting of codeine, morphine, hydrocodone, hydromorphone, levorphanol, propoxyphene, aspirin, ketorolac, ibuprofen, ketoprofen, flurbiprofen, etodolac, diclofenac, misoprostol, meloxicam, piroxicam, naproxen, caffeine, doxylamine, pamabrom, tramadol, dextropropoxyphene, methylhexital, carisoprodol, butalbital, diazepam, lorazepam, and midazolam.

5. A method of treating pain, fever, ischemic injury, or neuronal injury, comprising administering to an individual an effective amount of the compound of claim 1, or a pharmaceutically acceptable salt thereof.

6. The method according to claim 5, wherein the compound is administered orally.

7. The method according to claim 5, wherein the compound is administered parenterally.

8. A kit comprising the compound of claim 1 or a pharmaceutically acceptable salt thereof; and instructions for use in the treatment of pain, fever, ischemic injury, or neuronal injury.

9. The formulation of claim 2, wherein the formulation is a low volume/high concentration formulation comprising the compound of claim 1, or a pharmaceutically acceptable salt thereof, and a pharmaceutically acceptable carrier.

* * * * *